(12) United States Patent
Allaker et al.

(10) Patent No.: US 9,011,935 B2
(45) Date of Patent: Apr. 21, 2015

(54) THERAPEUTIC COMPOSITION AND USE

(75) Inventors: Robert Allaker, Teddington (GB); Charles Hinds, London (GB); Arthur Tudor Tucker, London (GB)

(73) Assignees: Barts Health National Health Service Trust (GB); Queen Mary and Westfield College (GB)

( * ) Notice: Subject to any disclaimer, the term of this patent is extended or adjusted under 35 U.S.C. 154(b) by 1153 days.

(21) Appl. No.: 12/226,331

(22) PCT Filed: Apr. 12, 2007

(86) PCT No.: PCT/EP2007/053591
§ 371 (c)(1),
(2), (4) Date: Feb. 13, 2009

(87) PCT Pub. No.: WO2007/116102
PCT Pub. Date: Oct. 18, 2007

(65) Prior Publication Data
US 2009/0317492 A1   Dec. 24, 2009

(30) Foreign Application Priority Data

Apr. 12, 2006   (GB) .................................. 0607402.5

(51) Int. Cl.
*A61K 33/00* (2006.01)
*A61P 31/00* (2006.01)

(52) U.S. Cl.
CPC ....................................... *A61K 33/00* (2013.01)
USPC ........................................................ 424/718

(58) Field of Classification Search
None
See application file for complete search history.

(56) References Cited

U.S. PATENT DOCUMENTS

| | | | |
|---|---|---|---|
| 4,678,670 A * | 7/1987 | Tomic | 424/718 |
| 5,396,882 A | 3/1995 | Zapol | 128/200.14 |
| 5,583,101 A * | 12/1996 | Stamler et al. | 424/718 |
| 5,648,101 A | 7/1997 | Tawashi | 424/718 |
| 5,713,349 A | 2/1998 | Keaney | 128/204.23 |
| 5,839,433 A | 11/1998 | Higenbottam | 128/204.21 |
| 6,187,332 B1 | 2/2001 | Gern et al. | 424/434 |
| 6,197,762 B1 | 3/2001 | Garvey et al. | 514/174 |
| 6,277,891 B1 | 8/2001 | Sanders et al. | |
| 6,645,948 B2 * | 11/2003 | Petito et al. | 514/62 |

(Continued)

FOREIGN PATENT DOCUMENTS

| | | | | |
|---|---|---|---|---|
| EP | 2012805 | * | 4/2013 | |
| WO | WO94/00180 | | 1/1994 | A61M 31/00 |

(Continued)

OTHER PUBLICATIONS

Nutrition Facts V8 vegetable juice [online] retrieved from http://nutritiondata.self.com/facts/vegetables-and-vegetable-products/10450/2?print=true on 2/4/11; 2 pages.*

(Continued)

*Primary Examiner* — Ernst V Arnold
*Assistant Examiner* — Jianfeng Song
(74) *Attorney, Agent, or Firm* — Egan, Peterman & Enders LLP.

(57) ABSTRACT

The use of liquid formulations in the preparation of a medicament for the prevention and treatment of oral, gastric and digestive infections and in particular for the prevention of ventilator associated pneumonia as well as liquid enteral and parenteral tube feeding compositions. The feeding compositions are suitable for use in the prevention of ventilator associated pneumonia.

11 Claims, 23 Drawing Sheets

(56) References Cited

U.S. PATENT DOCUMENTS

2004/0120938 A1    6/2004  Blake et al.
2004/0202754 A1*  10/2004  Sumimura et al. ............ 426/239

FOREIGN PATENT DOCUMENTS

| WO | WO95/09612 |   | 4/1995 | ............ A61K 9/127 |
|----|------------|---|--------|-------------------------|
| WO | WO95/22335 |   | 8/1995 | ............ A61K 33/00 |
| WO | WO-9522335 | * | 8/1995 |                         |
| WO | WO99/58001 |   | 5/1998 |                         |
| WO | WO99/02148 |   | 1/1999 | ............ A61K 31/195 |
| WO | WO00/30659 |   | 6/2000 | ............ A61K 33/08 |
| WO | WO00/53193 |   | 9/2000 | ............ A61K 33/00 |
| WO | WO01/26547 A1 |  | 4/2001 | ............ A61B 5/08 |
| WO | WO01/80890 A2 |  | 11/2001 | ............ A61K 45/00 |
| WO | WO02/09727 |   | 2/2002 |                         |
| WO | WO02/17881 A2 |  | 3/2002 | ............ A61K 9/06 |
| WO | WO02/41924 A1 |  | 5/2002 | ............ A61K 31/04 |
| WO | WO03/032928 A2 |  | 4/2003 | ............ A61K 7/00 |
| WO | WO2005/056102 |  | 6/2005 |                         |

OTHER PUBLICATIONS

Shikora (Nutritional Considerations in the Intensive Care Unit: science, rationale and practice; 2002, pp. 375-376) 4 pages.*

Maselli et al., "Strategies in the Prevention of Ventilator-associated Pneumonia", The Adv Resp Dis. 2011; 5(2): 131-141.*

Andresen, Max et al., "*Nitric Oxide in Respiratory Diseases*," 1977, Journal; General Review, Revista Medica de Chile, Sociedad Medica de Santiago.

Beghetti, Maurice et al., "*Recent Developments in Inhaled Nitric Oxide Therapy*," 1995, Journal; General Review, Expert Opinion on Investigation Drugs, Ashley Publications.

Cutherbertson, B.H. et al., "*Effect of Exogenous Nitric Oxide and Superoxide on Interleukin-8 from Human Polymorphonuclear Leukocytes*," 1977, Journal; British Journal of Anaesthesia, Professional and Scientific Publications.

Fang, Ferris C., "*Mechanisms of Nitric Oxide-Related Antimicrobial Activity*," Jun. 1997, vol. 99; No. 12; pp. 2818-2825, Perspectives Series: Host/Pathogen Interactions.

Heyder, J. et al., "*Deposition of Particles in the Human Respiratory Tract in the Size Range 0.005-15 $\mu m$*," 1986, J. Aerosol Sci., vol. 17, No. 5, pp. 811-825.

Hurford, William E., "*Clinical Therapy With Inhaled Nitric Oxide in Respiratory Diseases*," 2000, Nitric Oxide.

Wink, D.A. et al., "*Review: The Role of Nitric Oxide Chemistry in Cancer Treatment*," Jul. 4, 2004, 1-12 pp, Radiation Biology Branch, National Cancer institute; Cardiology Research Foundation.

Search Report, WO2007/116102A3, Oct. 18, 2007, 6 pgs.

McMullin et al., "The Antimicrobial Effect of Nitric Oxide on the Bacteria that Cause Nosocomial Pneumonia in Mechanically Ventilated Patients In The Intensive Care Unit", Respiratory Care, vol. 50, No. 11, Nov. 2005, 6 pgs.

Duncan et al., "Protection Against Oral And Gastrointestinal Diseases: Importance Of Dietary Nitrate Intake, Oral Nitrate Reduction And Enterosalivary Nitrate Circulation", Comp. Biochem. Physiol. vol. 118A, No. 4, 1997, 10 pgs.

* cited by examiner

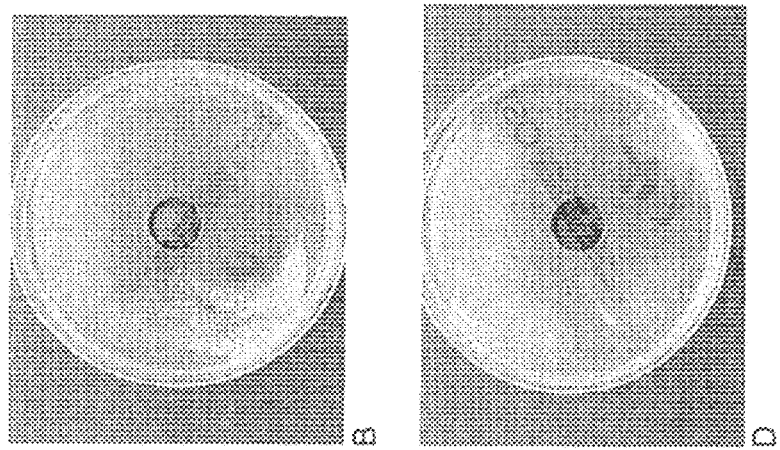
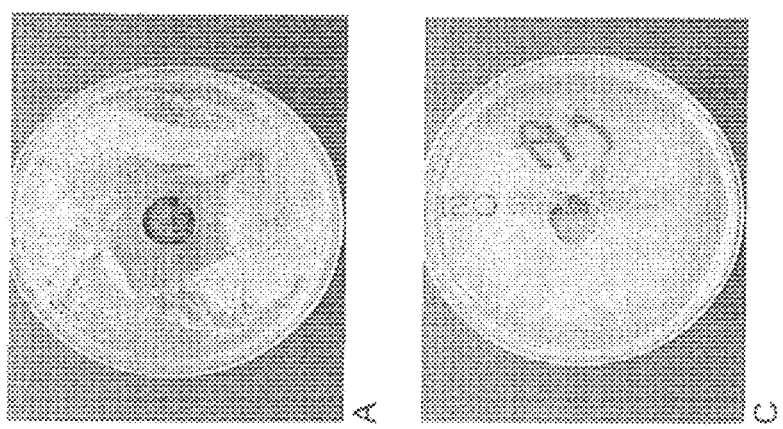
Figure 2

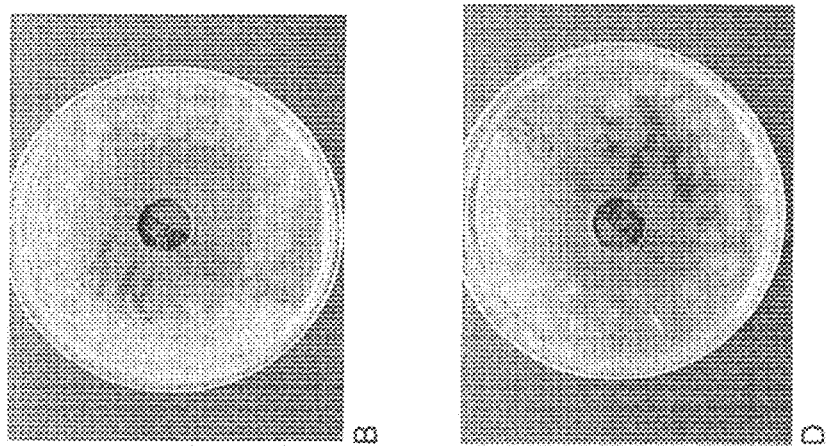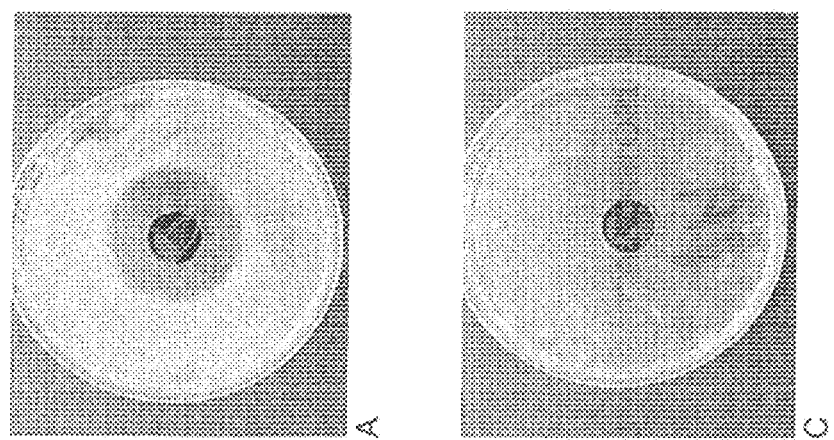
Figure 3

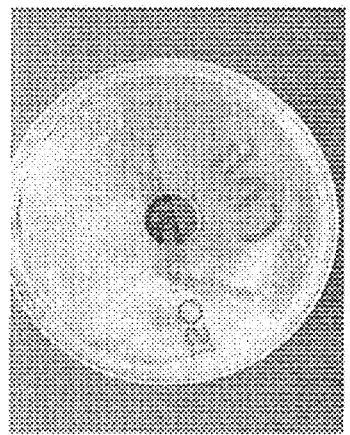
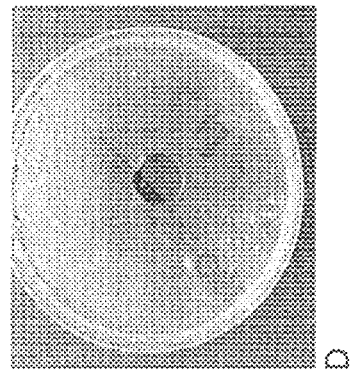
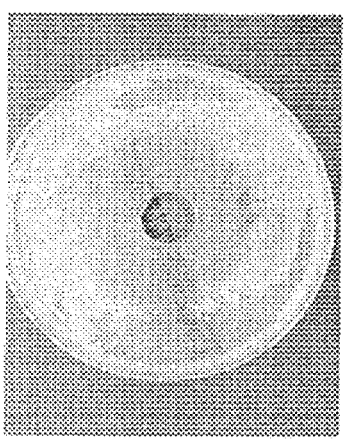
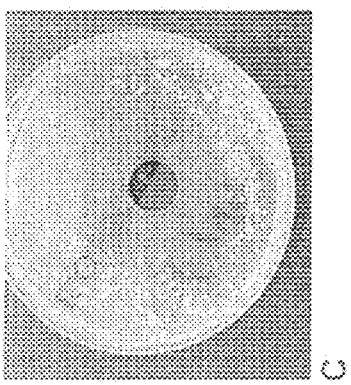
Figure 4

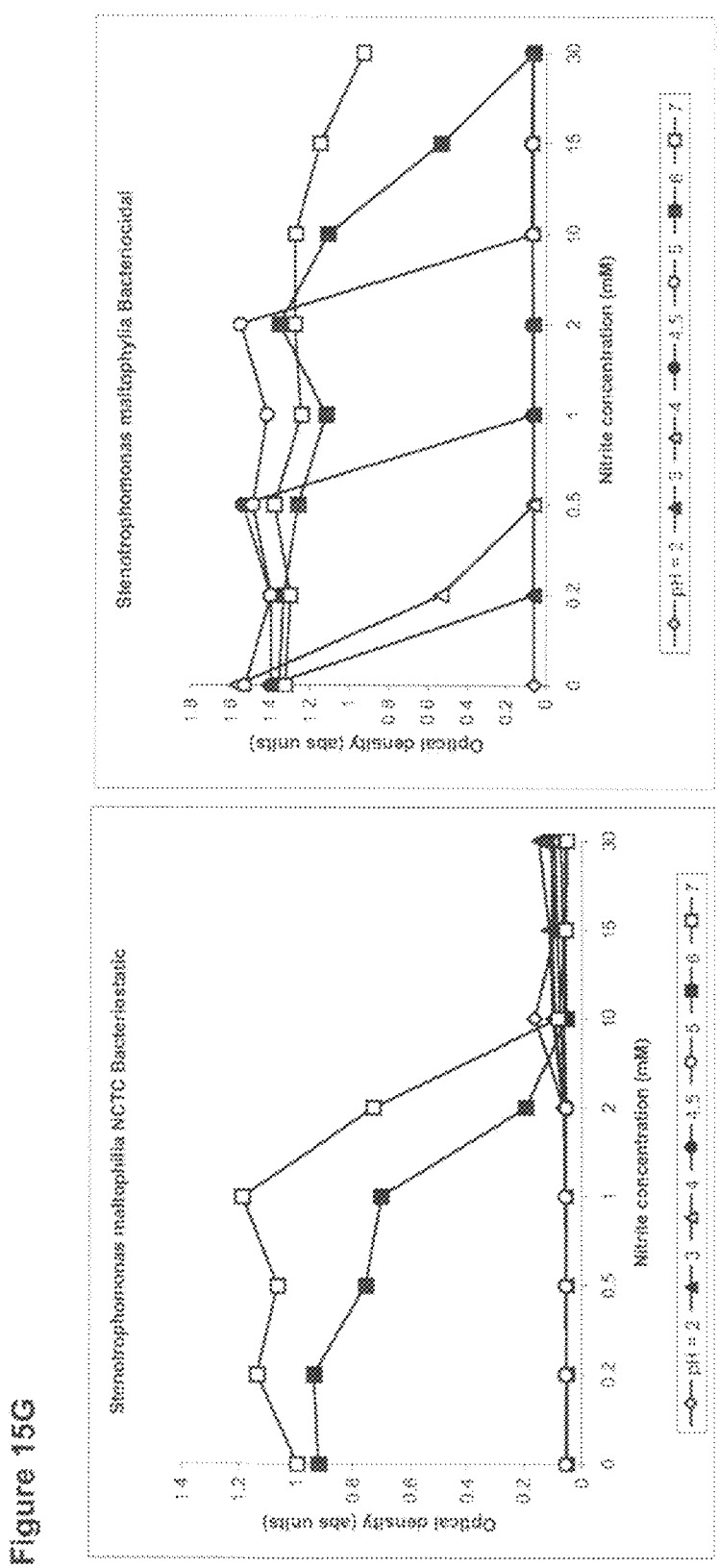

THERAPEUTIC COMPOSITION AND USE

The present invention relates to the use of liquid formulations in the preparation of a medicament for the prevention and treatment of oral, gastric and digestive infections and in particular for the prevention of ventilator associated pneumonia as well as liquid enteral tube feeding compositions. The feeding compositions are suitable for use in the prevention of ventilator associated pneumonia.

Nitric oxide is formed naturally in the stomach from a reaction of nitrite in saliva in combination with the acid in the stomach.

The production of NO from nitrite is believed to be through the following mechanism:

$$NO2^- + H^+ \Leftrightarrow HNO_2 \qquad [1]$$

$$2HNO_2 \Leftrightarrow N_2O_3 + H_2O \qquad [2]$$

$$N_2O_3 \Leftrightarrow NO + NO_2 \qquad [3]$$

It is thought that the gastric acid in the stomach may not be sufficient to destroy micro-organisms, and therefore that the production of NO in the stomach may assist with killing these micro-organisms (McKnight et al, Chemical synthesis of nitric oxide in the stomach from dietary nitrate in humans. Gut 1997; 40(2):211-4).

There has been much interest in recent years in pharmaceutical applications of nitric oxide [NO] and nitric oxide precursors. Nitric oxide has been shown to possess anti-microbial properties, reviewed by F. C. Fang (1997) (*J. Clin. Invest.* 99 (12) 2818-2825 (1997)).

It has been found in WO03/032928 that it is possible to formulate solutions in which a clinically effective amount of nitric oxide is dissolved or dispersed therein. These solutions are then nebulised for spraying into the lungs for treatment of certain respiratory diseases.

There are a number of other disclosures which also deal with the artificial provision of nitric oxide.

WO 95/22335 (Benjamin & Dougal) discloses a dosage form for the treatment of bacterial, virus, or fungal conditions which comprises a pharmaceutically acceptable acidifying agent, a pharmaceutically acceptable source of nitrite ions or a nitrate precursor therefor, and a pharmaceutically acceptable carrier or diluent, wherein the acidifying agent is adapted to reduce the pH at the environment of use to below pH 4. Preferably the acidifying agent is an organic acid, for example salicylic acid or ascorbic acid. The precursor for the nitrite ion may be an alkaline metal or alkaline earth metal capable of conversion to a nitrate by enzymatic action. In a particularly preferred form of the invention the acidifying agent and the source of nitrite ions or precursor therefore are separately disposed in said cream or ointment for the admixture to release nitrite ions at the environment of use. Alternatively an acid composition may be presented for administration in tablet or liquid form.

U.S. Pat. No. 5,648,101 (Tawashi) discloses a method for delivering NO gas to a desired site or into the body of a sentient animal, e.g. humans, comprising combining and causing to react a soluble reducing salt, preferably ferrous sulphate, and a nitrite, preferable sodium nitrite in the presence of moisture in situ at or adjacent to such a site. Means for such delivery include compositions such as tablets, capsules, ointments, creams, lotions and sprays containing mixtures of particles or granules of the two reactants, transdermal patches and osmotic pumps for combining solutions of reactant or reactants in situ.

Wink et al, The role of nitric oxide chemistry in cancer treatment, (Biochemistry (Moscow) 802-809; 63(7):1998) discloses the effect of nitric oxide upon mammalian tumours. Current disclosures in the field of cancer treatment refer to endogenous production of nitric oxide. Attempts to increase local availability have been limited to non-direct interventions such as dosing with nitric oxide precursors (L-arginine) and manoeuvres to increase the half-life/bioavailability of endogenous nitric oxide by temporarily modulating breakdown pathways.

Other clinical methods involving the use of NO precursors are disclosed in WO-A-99/02148, WO-A-95/09612 and Chemical Abstracts; 127:130755, B. H. Cuthbetson et al, British Journal of Anaesthesia, (1977), 78(6), 714-717.

The topical use of gaseous nitric oxide and nitric oxide precursors as antimicrobials is also known. WO-A-01/53193 discloses the use of acidified nitrite to produce nitric oxide topically at the skin surface. The treatment is useful in the treatment of ischaemia and related conditions.

In topical application to the skin of nitrite at concentrations of up to 20% in an inert carrier cream or ointment, the nitrite, when mixed with an organic acid such as ascorbic acid (vitamin C), reacts to produce oxides of nitrogen to cause the release of nitric oxides leading to sustained vasodilation of the microcirculatory blood vessels, without significant inflammation.

Useful reviews of the use of NO in therapy are provided in the following review articles;

Chemical Abstracts; 134:216558, W. E. Hurford et al, Nitric Oxide, (2000), 931-945;

Chemical Abstracts; 128:21192, M. Andresen et al, Revista Medica de Chile, (1997), 125 (8) 934-938;

Chemical Abstracts; 124:44545, M. Beghetti et al, Expert Opinion on Investigational Drugs, (1995),4 (10) 985-995.

Ventilator associated pneumonia (VAP) is a nosocomial infection occurring in patients who have been mechanically ventilated for more than 48 hours (Young et al. 1999). Early onset VAP occurs between 48 and 72 hours after instituting mechanical ventilation and is thought to result from aspiration during the process of tracheal intubation. VAP developing beyond this time is considered to be late onset. The reported incidence of VAP varies from around 10% to more than 30%, depending on case-mix and the diagnostic criteria. VAP is the most prevalent infection in European intensive care units and accounts for almost half of all infections acquired in the ICU. The development of VAP prolongs intensive care and hospital stay and increases costs. In patients with acute respiratory distress syndrome (ARDS), for example the occurrence of VAP was responsible for a nearly three-fold increase in the duration of mechanical ventilation (Markowicz et. al 2000). Although controversial, many believe that the development of VAP also independently increases mortality (the mortality directly attributable to VAP has been estimated at about 27%). Therefore, new interventions are urgently required to reduce the considerable morbidity and mortality associated with VAP, as well as to reduce costs, particularly in view of the increasing resistance of bacterial pathogens to traditional antimicrobial treatment (Bonten et al: Bird's eye view of nosocominal infections in medical ICU: blue bugs, fungi, and device days. Crit Care Med 1999, 27:853-854; Bonten: Prevention of the infection in the Intensive Care Unit. Current Opinion in Critical Care, 2004, 10:364-368; Richards M J, Edwards J R, Culver D H, et al: Nosocominal infections in medical intensive care units in the United States. National nosocomial infections surveillance system. Crit Care Med 1999, 27:887-892).

The development of late onset VAP is usually a consequence of aspiration of infected secretions from the aerodigestive tract into the distal airway. Whereas in health the oropharynx is colonised by non-pathogenic bacteria and the stomach is sterile, during critical illness the stomach, oropharynx, peridontal areas and sinuses become colonised with pathogenic organisms, including aerobic gram-negative bacteria, *staphylococcus* spp. and *pseudomonas* spp. Subsequently infected secretions pooling in the oropharynx and the laryngeal opening leak past the cuff of the tracheal tube and are dispersed distally. The almost invariable presence of a nasogastric tube is thought to predispose patients to gastric reflux and increase the potential for aspiration. Moreover the inner lumen of the tracheal tube rapidly develops a viscous, adhesive layer of accretions containing pathogenic organisms ('biofilm'), particles of which may be dislodged and propelled deeper into the lungs. On the other hand direct inoculation from contaminated respiratory apparatus or the ventilator circuit is thought to be an unusual cause of VAP. The vulnerability of mechanically ventilated patients to the development of nosocomial pneumonia is further increased by compromised defense mechanisms, including impaired cough and decreased muco-ciliary clearance. Mucosal injury at the level of the tracheal tube cuff and tip (perhaps exacerbated by aspiration of bile and gastric fluid) and damage to the mucosa by suction catheters exposes the basement membrane, thereby facilitating bacterial adhesion and colonisation. Finally alveolar damage and loss of surfactant further impair lung defenses.

Accordingly, it would be advantageous if a new method of preventing development of VAP could be found.

In a first aspect of the present invention, there is provided the use of a liquid formulation comprising an clinically effective amount of oxides of nitrogen dissolved and/or dispersed therein in the preparation of a medicament for the prevention of ventilator associated pneumonia, or for the prevention and/or treatment of infections of at least one of the oropharynx, the gastric system and the digestive system.

Preferably, there is provided the use of a liquid formulation comprising a clinically effective amount of oxides of nitrogen dissolved and/or dispersed therein in the preparation of a medicament for the prevention of ventilator associated pneumonia.

It has been found that in mechanically ventilated patients, there is a large reduction in the production of gastric nitric oxide. Without wishing to be bound by theory, we consider that this reduction in production of gastric nitric oxide allows an increase in bacterial colonisation of the stomach contents. This predisposes the patient to VAP, especially when combined with the alkalisation of gastric secretions by H2 receptor antagonists.

What has now been found is that a liquid formulation which comprises oxides of nitrogen dissolved and/or dispersed therein are useful in the prevention of the spread of the bacteria to the lungs.

Most mechanically ventilated patients are fed using an enteral tube. Therefore, a suitable method of feeding the oxides of nitrogen containing liquid formulation into the stomach is via an enteral tube. A preferred method of feeding the oxides of nitrogen into the stomach is therefore the use of a liquid feeding composition which comprises the oxides of nitrogen.

In a second aspect of the present invention, there is provided a liquid enteral tube feeding composition comprising both a clinically effective amount of oxides of nitrogen dissolved and/or dispersed therein and at least one nutrient.

The feeding composition allows the oxides of nitrogen to be fed directly into the stomach. In addition, the feeding composition can also prevent microbial (bacterial, fungal, protozoan and viral) formation on the inside of the enteral tube. Such colony formation can easily occur because the liquid nutrient feed provides a particularly good environment for such bacteria to grow.

The nutrient containing solution preferably contains variable calorific content, protein, glucose, fat, water, electrolytes, trace elements and vitamins; but may be varied according to clinical indication. Enteral feeds can be classified into three categories: chemically defined diets, specifically formulated diets, and Standard polymeric diets. Chemically defined or elemental diets contain nutrients that require little or no digestion and hence are easily absorbed. Specially formulated diets are those designed to overcome a specific problem in digestion such as lactose intolerance. The standard polymeric diet has whole protein rather than amino acids as the nitrogen source and is appropriate where there is normal or near normal gastrointestinal function. Preparations suitable for tube feeding are usually one of three types: normal food that has been put through a blender and sieved, reconstituted powder preparations which require the addition of water or milk, and ready-to-feed products. It is particularly preferred that the nutrient feed is a commercially available liquid enteral feeding composition such as that sold under the trade name Osmolite®.

The liquid formulations of the present invention, and particularly the feeding composition can additionally comprise other components. By the addition of these components, the adherence, duration of contact and the extent of the desired biological action of the liquid formulations may be increased. Preferred additional components include foaming agents (such as soap and detergents), for reducing the drift of the discharged system in situ. Other preferred additional components include gelling agents (for increasing viscosity), thickeners (for increasing droplet size), spreaders (for enhancing even coating of a target surface), stabilizers and buffers (for maintaining integrity of the system and enhancing effective combination with additional agents), and surfactants (for increasing wettability of a target surface).

In a further aspect of the present invention, there is provided a liquid parenteral feeding composition comprising a clinically effective amount of oxides of nitrogen dissolved and/or dispersed therein and at least one nutrient.

A parenteral feeding composition commonly comprises dextrose, amino acids and water. A typical solution contains 25-35% dextrose and 2.75-6% amino acids together with minerals, vitamins and trace elements and fat emulsion (20%). Usually it is provided at 30 ml/hour on day 1 and 60 ml/hour on day 2. This composition provides adequate protein but usually inadequate energy that must be supplemented with IV lipids. IV fat is increasingly used in patients with large energy requirements to prevent excess administration of dextrose In a further aspect of the present invention, there is provided the use of a liquid formulation comprising a clinically effective amount of oxides of nitrogen dissolved and/or dispersed therein in the preparation of a medicament for the prevention and/or treatment of infections of at least one of the oropharynx, the gastric system and the digestive system.

The liquid formulation is useful not only for the prevention of VAP, but also for the prevention of infection in oropharynx, the gastric system or the digestive system. Furthermore, the liquid formulation can also be used to treat infections of the oropharynx, the gastric system or the digestive system.

The oxides of nitrogen may be present in the liquid formulations according to the invention in true solution, and/or in the form of a dispersion or suspension (for example in colloidal suspension). All such formulation types are referred to herein as "solutions".

The oxides of nitrogen which are present comprise nitric oxide. However, other oxides of nitrogen may also be present in the mixture. A range of oxides of nitrogen are usually present.

In such liquid formulations, the effective compositions will generally contain concentrations of dispersed and/or dissolved NO in the range of from 10 to 40,000 ppb (parts per billion) by weight, preferably from 100 to 10,000 ppb, more preferably from 1,000 to 10,000 ppb.

The liquid formulations employed in accordance with the present invention may be prepared by the use of a pharmacologically acceptable acidifying agent, together with a pharmacologically acceptable source of nitrite ions or a nitrite precursor. It is preferred that the nitric oxide is dissolved or suspended in a liquid, either by passing gaseous NO through a liquid, or by generating NO in situ in the liquid.

It is preferred that the NO is generated in the liquid in situ by the reaction of at least one nitrite and at least one acid. For example, the NO can be produced in aqueous solution by the reaction of 0.5 molar nitrite with 0.5 molar citric acid, which results in a concentration of NO dispersed or dissolved in the liquid formulation, after gas evolution, of the order of 1,500 ppb (1.5 ppm). Additionally, the resulting liquid formulation remains stable within a time span required for use to prevent ventilator associated pneumonia (for example, for periods in excess of one hour).

A preferred method of NO generation is the reaction of $NaNO_2$ and $KNO_2$ with ascorbic acid. It is particularly preferred that equimolar amounts of $NaNO_2$ and $KNO_2$ are used. In one favourable embodiment, the NO is generated by a reaction of a volume of 1M $NaNO_2$ and an equal volume of 1M $KNO_2$ with twice the volume of 1M ascorbic acid.

The pH of the resulting liquid formulation may be manipulated by the titration of the acidifying agent and/or subsequent chemical buffering using standard techniques to create a pharmaceutically acceptable formulation.

The acidifying agent may include any suitable organic acid such as ascorbic acid (vitamin C), salicylic acid, acetyl salicylic acid, acetic acid or a salt or a derivative thereof, generally in a concentration up to 20% w/v, preferably 0.25 to 10% w/v, more preferably 4 to 6% w/v. A particularly preferred concentration is 4% or 5% w/v. Other acidifying agents include but are not limited to, ammonium or aluminium salts, phenol, and benzoic acid. Inorganic acids such as hydrochloric acid may be used if sufficiently dilute and/or appropriately buffered. The acidifying agent may be present as a dissolved salt or in a liquid form.

The pharmacologically acceptable source of nitrite ions may an alkaline metal nitrite or an alkaline earth metal nitrite, for example, $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, or $Ra(NO_2)_2$. Alternatively, a nitrite precursor may be used as the source of the nitrite ions in the composition, such as for example a dilute solution of nitric acid. Other sources of nitrite ions are nitrate ions derived from alkali metal or alkaline earth metal salts capable of enzymic conversion to nitrite, For example, $LiNO_3$, $NaNO_3$, $KNO_3$, $RbNO_3$, $CsNO_3$, $FrNO_3$, $Be(NO_3)_2$, $Mg(NO_3)_2$, $Ca(NO_3)_2$, $Sr(NO_3)_2$, $Ba(NO_3)_2$, or $Ra(NO_3)_2$. The concentration of the nitrate ion source prior to acidification may be up to 20% w/v, suitably 0.25 to 10%, preferably 4 to 6%. A particularly preferred concentration is 4% or 5% w/v.

The liquid formulation employed in accordance with the invention is preferably saturated with nitric oxide in solution.

Features described in connection with one aspect of the invention can also be used in connection with other aspects of the invention.

BRIEF DESCRIPTION OF THE DRAWINGS

Preferred embodiments of the invention will now be further described with reference to the drawings in which:

FIG. 2 shows agar plates containing *Candida Albicans* treated with:
A—ascorbic acid
B—premixed ascorbic acid, $NaNO_2$ and $KNO_2$
C—$NaNO_2$ followed by ascorbic acid and
D—$KNO_2$ followed by ascorbic acid;

FIG. 3 shows agar plates containing *Pseudomonas Aeruginosa* treated with:
A—ascorbic acid
B—premixed ascorbic acid, $NaNO_2$ and $KNO_2$
C—$NaNO_2$ followed by ascorbic acid and
D—$KNO_2$ followed by ascorbic acid;

FIG. 4 shows agar plates containing Coagulase Negative *Staphylococcus* treated with:
A—ascorbic acid
B—premixed ascorbic acid, $NaNO_2$ and $KNO_2$
C—$NaNO_2$ followed by ascorbic acid and
D—$KNO_2$ followed by ascorbic acid;

EXAMPLES

Figure 1:
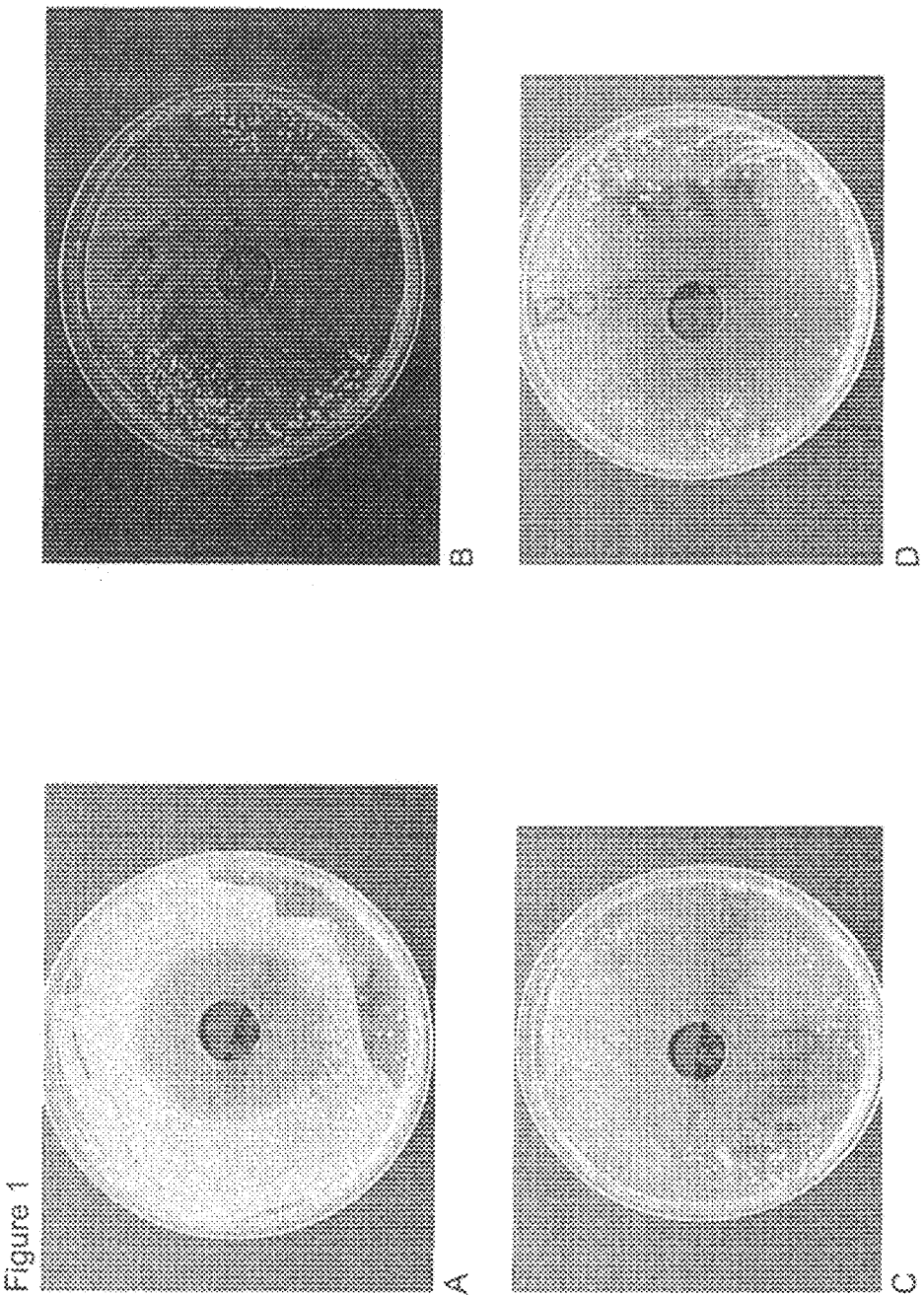
FIG. 1 shows agar plates containing Methicillin Resistant *Staphylococcus Aureus* treated with:
A—ascorbic acid
B—premixed ascorbic acid, $NaNO_2$ and $KNO_2$
C—$NaNO_2$ followed by ascorbic acid and
D—$KNO_2$ followed by ascorbic acid.

A number of Examples were set up to test the efficacy of solutions containing oxides of nitrogen at killing bacteria.

Examples 1 to 4

A premixed "oxides of nitrogen" generating solution was prepared by acidification of sodium nitrite (NaNO2) and potassium nitrite (KNO2) with ascorbic acid. A 1M solution of sodium nitrite was prepared by dissolving 6.9 g of $NaNO_2$ in 100 ml of distilled water. A 1M solution of potassium nitrite was prepared by diluting 8.51 g of $KNO_2$ in 100 ml of distilled water. 17.612 g of ascorbic acid was diluted in 100 ml of distilled water to form a 1M solution. The three stock solutions were prepared a few minutes prior to the experiments.

A volume of NaNO$_2$ and an equal volume of KNO$_2$ were mixed with twice the volume of ascorbic acid in a sterile container to produce an "oxides of nitrogen" containing solution. A reaction between the nitrites and the acid occurred instantly. The gas produced was released and 2 ml of the premixed liquid (0.25M) was added to 20 ml of distilled water to give a final concentration of the solution of 1.25 mM.

Separate samples of NaNO$_2$, KNO$_2$ and ascorbic acid were also prepared as described above.

The antibacterial effect of:

A) ascorbic acid alone,

B) the premixed "oxides of nitrogen" generating solution,

C) a combination of separately added NaNO$_2$ and ascorbic acid and

D) a combination of separately added KNO$_2$ and ascorbic acid were measured by testing on:

Example 1—Methicillin Resistant *Staphylococcus Aureus* (MRSA),

Example 2—*Candida Albicans* (CA),

Example 3—*Pseudomonas Aeruginosa* (PS), and

Example 4—Coagulase negative *Staphylococcus* (CNS).

An overnight culture of bacteria was prepared by inoculating 20 ml of LB (Luria-Bertani 10 g Bacto-tryptone, +5 g Bacto-yeast extract, +10 g sodium chloride per liter, at pH 7.5) broth with 2 to 3 colonies, and incubating at 37° C. overnight. Broth cultures containing approximately 109 organisms were produced. Bacteria were diluted 1:1000 using phosphate buffer saline (PBS) and 100 µl of diluted broth cultures were seeded on the Brain-Heart agar plates. Prior to seeding bacteria on to the surface of the agar plates a piece of agar (approximately 70 mm in diameter) from the centre of the plates was removed.

In A), in order to test the bactericidal potency of 0.25M ascorbic acid, 50 ml of stock solution (1M) was further diluted. 280 µl of 0.25M ascorbic acid was added to the hollow circle of the agar plates seeded with the bacteria.

In B), 280 µl of the "oxide of nitrogen" generating solution (final concentration 0.25M) was added to the hollow circles on the agar plates.

In C) and D), the antibacterial effect of NO gas was tested by adding chemicals separately rather than premixing the solutions. In C), 140 µl (0.5M) of NaNO$_2$ was added to the agar plates, followed by 140 µl (0.5M) ascorbic acid. Reaction occurred and the agar plates were covered with the lid instantly. The same procedure was repeated in D) using KNO$_2$ and ascorbic acid.

The results are shown in FIGS. 1 to 4. It can be seen that for each of Examples 1 to 4, there is a large amount of bacteria where ascorbic acid only is used in A). However, in B, C and D, most of the bacterial colonies have been destroyed.

Example 5

A Methicillin Resistant *Staphylococcus Aureus* (MRSA) culture was produced in the same manner as for Examples 1 to 4. The agar plate was placed in a polystyrene box. Gaseous NO was produced by reacting 10 ml 1M ascorbic acid with 5 ml 1M NaNO$_2$ and 5 ml 1M KNO$_2$ in the box and the lid of the box replaced immediately, followed by overnight incubation of the culture.

Figure 5:
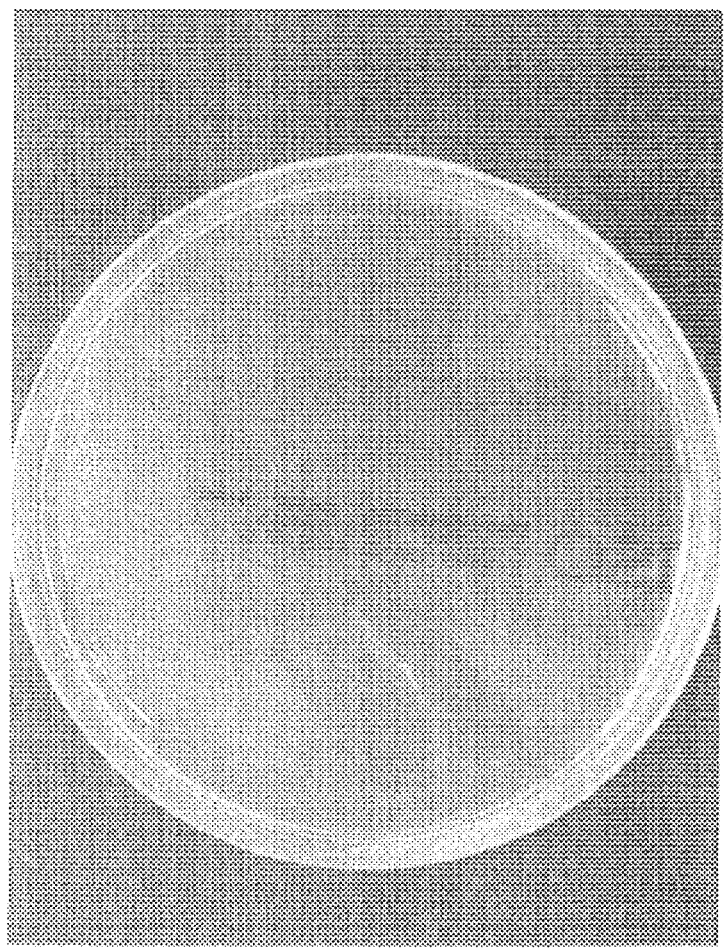
FIG. 5 shows an agar plate containing Methicillin Resistant *Staphylococcus Aureus* treated with nitric oxide gas.

The results are shown in FIG. 5. As can be seen, there are no remaining visible bacterial cultures.

Examples 6 to 10

Figure 6:
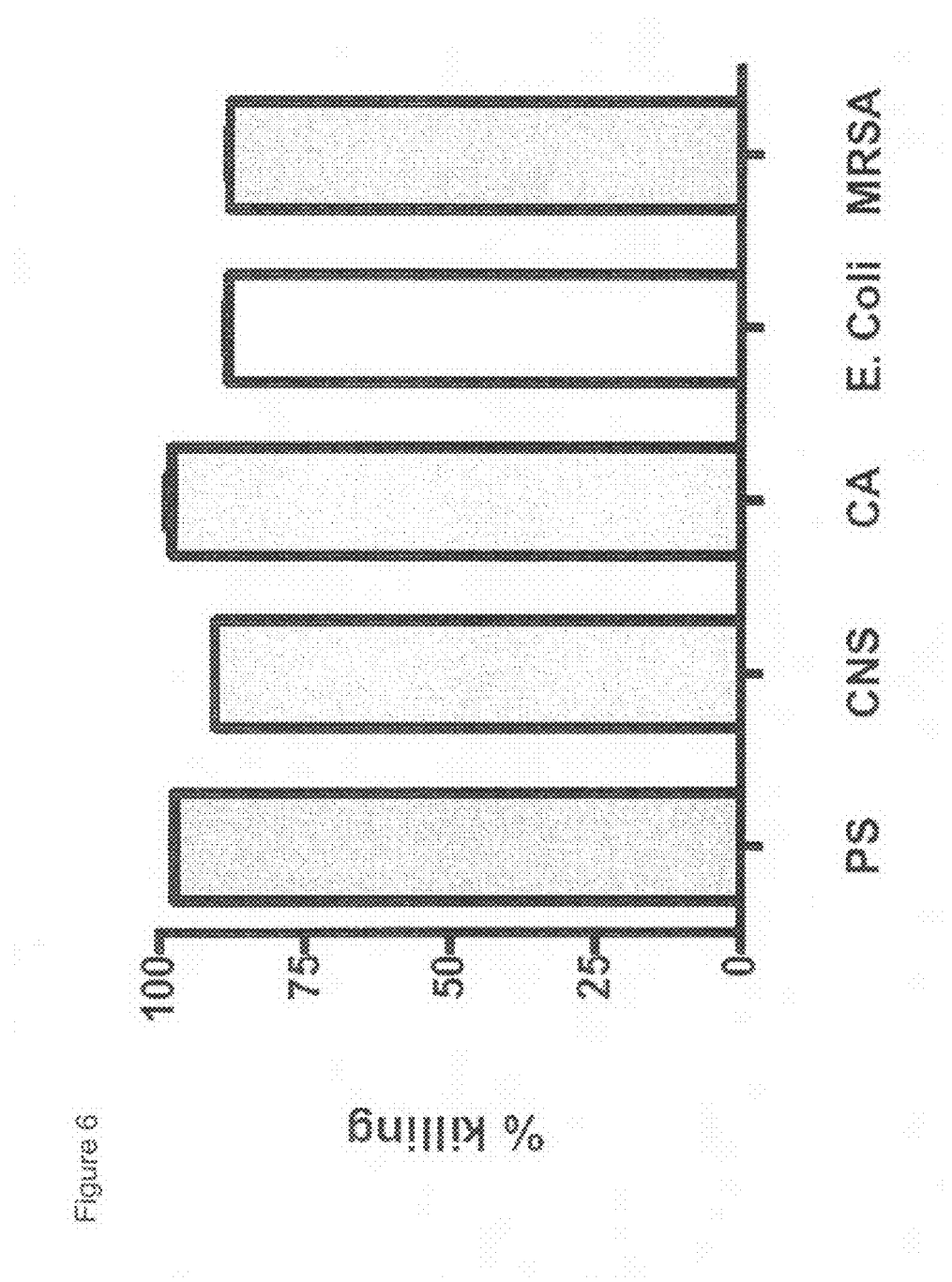
FIG. 6 shows the effect of an oxide of nitrogen containing mixture on a number of different strains of bacteria.

The bactericidal effect of oxides of nitrogen generating solution was tested under conditions simulating the stomach. FIG. 6 shows that exposure of bacteria to oxides of nitrogen generating solution for 1 hour did result in on average 97% killing in five different bacteria tested, namely *Pseudomonas Aeruginosa*; Coagulase negative *Staphylococcus*; *Candida albicans*; *Escherichia coli*; and *Staphylococcus Aureus*. The experimental design was identical to that described in Examples 1 to 4.

Examples 11 to 15

The oxides of nitrogen generating solution used in Examples 1 to 4 was used to test its anti-microbial activity in commercially available enteral feed Osmolite® used for patients nutrition in ICU. The effect of mixture was tested on *Pseudomonas Aeruginosa* (PS), Coagulase negative *Staphylococcus* (CNS), *Esherichia coli* (*E. Coli*) *Candida Albicans* and Methicillin Resistant *Staphylococcus Aureus*.

Overnight cultures of bacteria were prepared by inoculating 20 ml of LB (Luria-Bertani 10 g Bacto-tryptone, +5 g Bacto-yeast extract, +10 g sodium Chloride per liter, at pH 7.5) broth with 2-3 colonies, and incubating at 37° C. overnight. Broth cultures containing approximately 109 organisms were produced. Bacteria were diluted 1:1000 in phosphate buffer saline (PBS) and 100 µl of diluted broth cultures were placed in 20 ml of commercially available enteral feed Osmolite® used in ICU for patients nutrition.

2 ml of the premixed oxides of nitrogen generating solution was added to 20 ml of the bacteria containing Osmolite® giving a final concentration of the solution of 1.25 mM. The same volume of sterile water was used as control. Incubation of 20 ml of contaminated feed containing 2 ml of oxides of nitrogen generating mixture or sterile water was performed for 1 h at 37° C. Following 1 h incubation, samples of feed (100 µl) were placed on blood agar plates and spread using a sterile spreader. Plates were incubated for 20 h at 37° C. Numbers of colonies were counted and data expressed as a percentage killing or simply as comparison of number of visible colonies in treated and control group.

Figure 7:
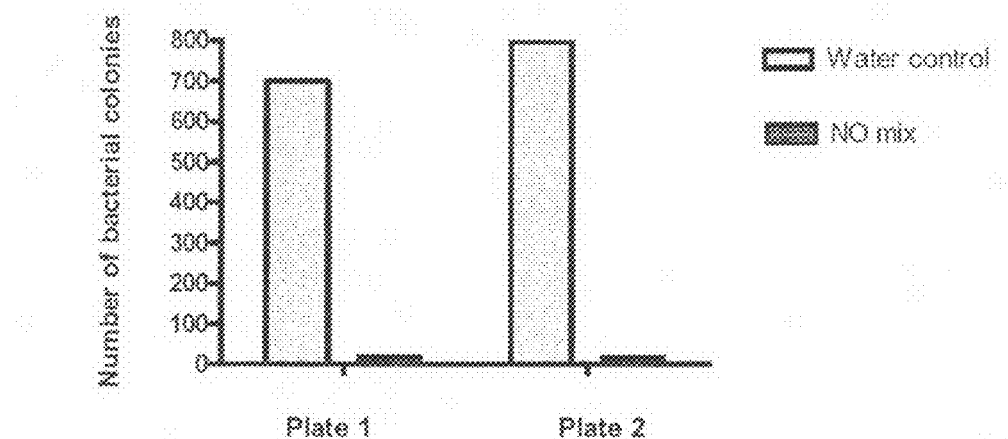
FIG. 7 shows the effect of a mixture of oxides of nitrogen in Osmolite® on *Pseudomonas Aeruginosa;*
Figure 8:
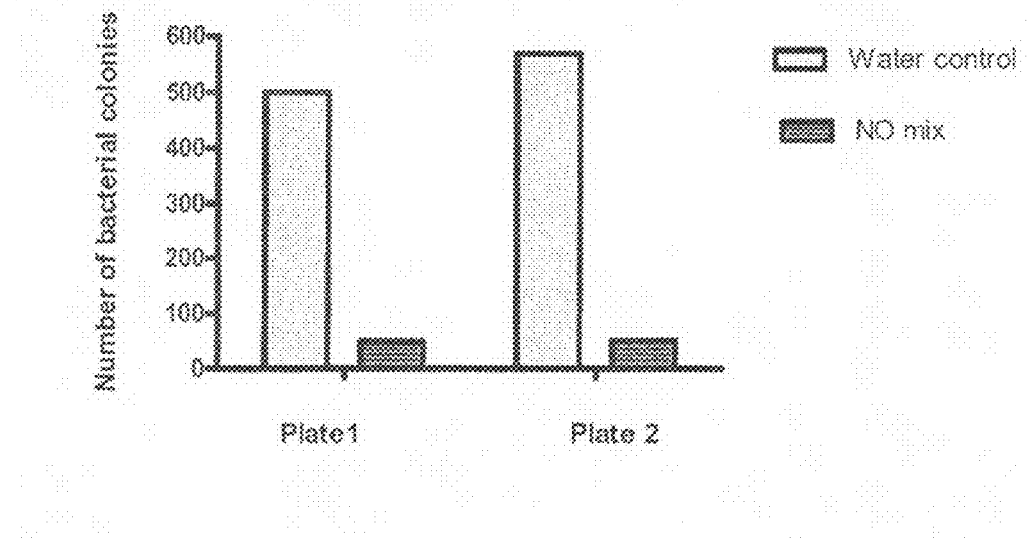
FIG. 8 shows the effect of a mixture of oxides of nitrogen in Osmolite® on Coagulase negative *Staphylococcus;*
Figure 9:
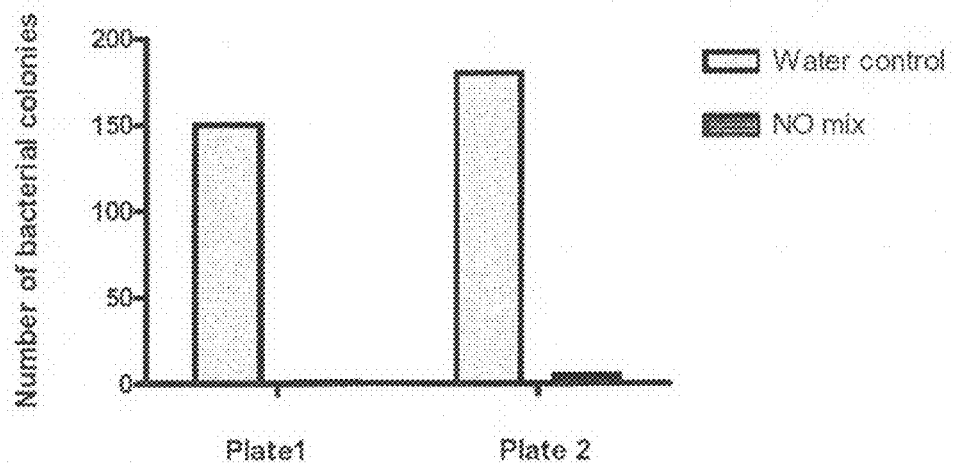
FIG. 9 shows the effect of a mixture of oxides of nitrogen in Osmolite® on *Candida albicans;*
Figure 10:
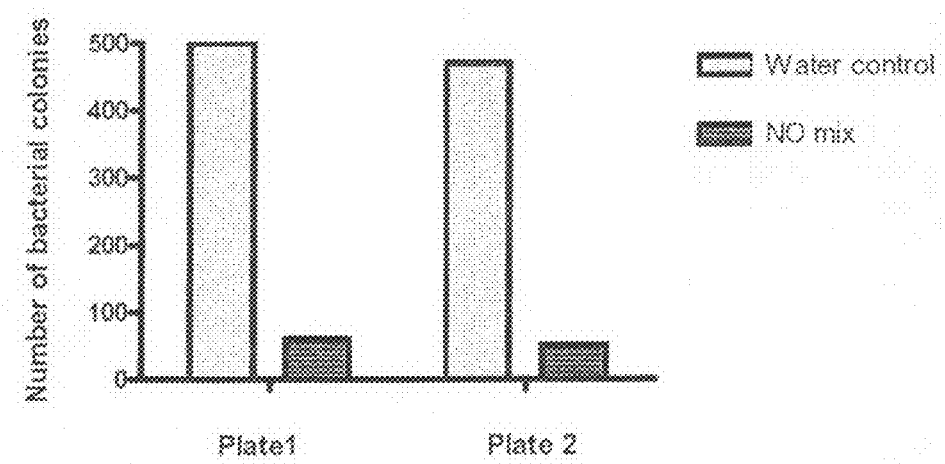
FIG. 10 shows the effect of a mixture of oxides of nitrogen in Osmolite® on *Escherichia coli.
Figure 11:
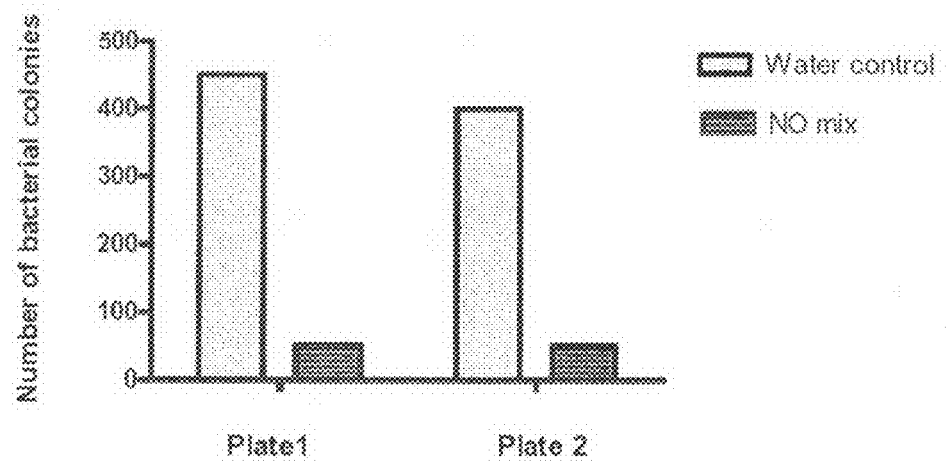
* and FIG. 11 shows the effect of a mixture of oxides of nitrogen in Osmolite® on methycilin resistant *Staphylococcus Aureus.*

The results are shown in FIGS. 7 to 11. FIG. 7 shows the effect on *Pseudomonas Aeruginosa*, FIG. 8 shows the effect on Coagulase Negative *Staphylococcus* (CNS), FIG. 9 shows the effect on *Candida Albicans*, FIG. 10 shows the effect on *Escherichia Coli* (*E. Coli*) and FIG. 11 shows the effect on Methicillin Resistant *Staphylococcus Aureus* (MRSA).

The results clearly demonstrate that the oxide of nitrogen containing mixture destroys most of the bacterial colonies.

The results show that the oxide of nitrogen containing solutions can be used safely for oropharyngeal hygiene of the patients.

It has also been found that where the nitrite and acid are not premixed, the nitrite can react with the feed to produce a precipitate. For example nitrite, followed by addition of ascorbic acid results in significant precipitation of the proteins, which increases the viscosity of the feed. For this reason the components must be premixed to produce oxides of nitrogen generating solution. Increased viscosity of the feed will substantially increase the known risks of catheter blockage.

Therefore, production of acidified nitrite by adding chemicals separately is not a formulation of choice in terms of development and prevention of a potential treatment. Moreover, unless premixed NO/NOx generating solution is used, already vulnerable patients on mechanical ventilation, usually receiving H2 inhibitors, might be exposed to an increased risk of developing a gastric ulcer.

Another benefit of the premixed oxides of nitrogen generating solution is that antibacterial effect is exhibited at a wider range of pH levels, i.e. not only below 5.0. Therefore, the solution can be used safely for oropharyngeal hygiene of the patients.

Furthermore, the residual components of the acidified nitrite reactions, in particular ascorbic acid (Vitamin C), have an individual nutritional and protective role. Vitamin C is a powerful water-soluble antioxidant, protecting low-density lipoproteins from oxidation, reducing harmful oxidants in the stomach (for example peroxinitrite free radicals) and promotes iron absorption.

Examples 16 and 17

The pH change was measured when L-ascorbic acid was added to sodium nitrite incrementally and as a single addition.

Analytical grade (>99% purity) sodium nitrite ($NaNO_2$) and L-ascorbic acid ($C_6H_8O_6$) from Sigma-Aldrich, UK were used. Saline (0.9% wv of NaCl) was from Baxter Healthcare-UK was also used.

Normal saline was used as solvent in the preparation of the solutions of sodium nitrite and ascorbic acid. All solutions were prepared at room temperature (22-25° C.) in lots of 25 or 50 ml and were used within 10-20 days. Stock solutions were kept in airtight vessels away from light.

All pH measurements of the solutions were carried out with a Wissenschaftlich-Technische Werkstätten (WTW) pH meter, model pH340i along with a SenTix 20 pH combination electrode incorporating a thermocouple. The electrode was calibrated with freshly prepared buffer calibrating solutions (pH 7.00 and 4.00±0.002). Calibrating solutions were prepared from ALDRICH Tri-check buffer capsules, Aldrich, USA.

The pH of the solutions was measured with the addition of a standard magnetic stir bar operating at 60 rpm. At least 12 ml of solutions were used to ensure that the electrode was completely immersed. 1M solutions of sodium nitrite and ascorbic acid were prepared using normal saline as solvent. In Example 16, 1 ml of acid was added to the nitrite every 10 minutes. In Example 17, 5 ml of 1M ascorbic acid were added to 12 ml of 1M sodium nitrite solution.

Figure 12:
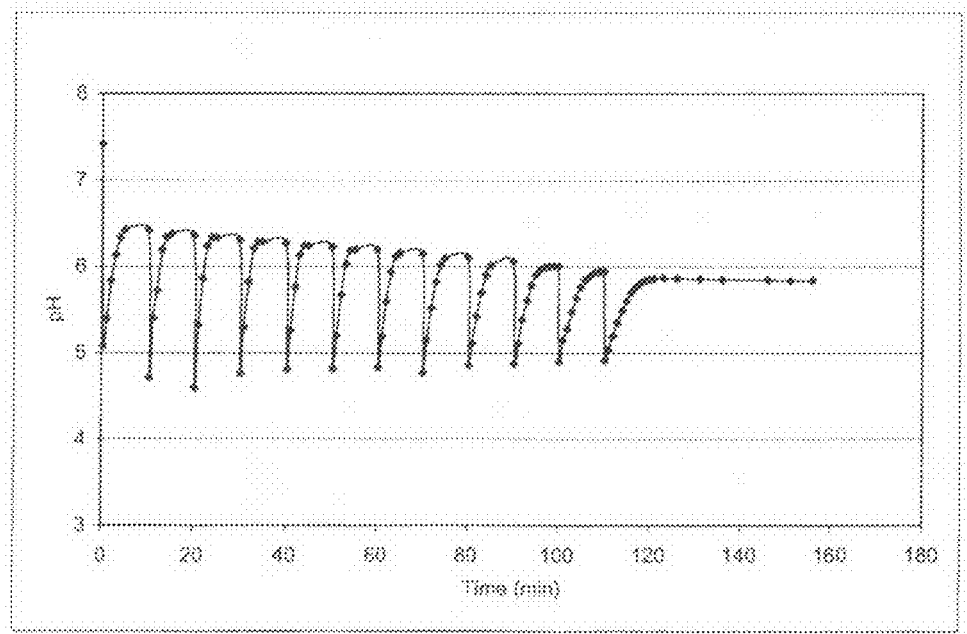
FIG. 12 shows the effect on pH of incremental addition of acid to nitrite.
Figure 13:
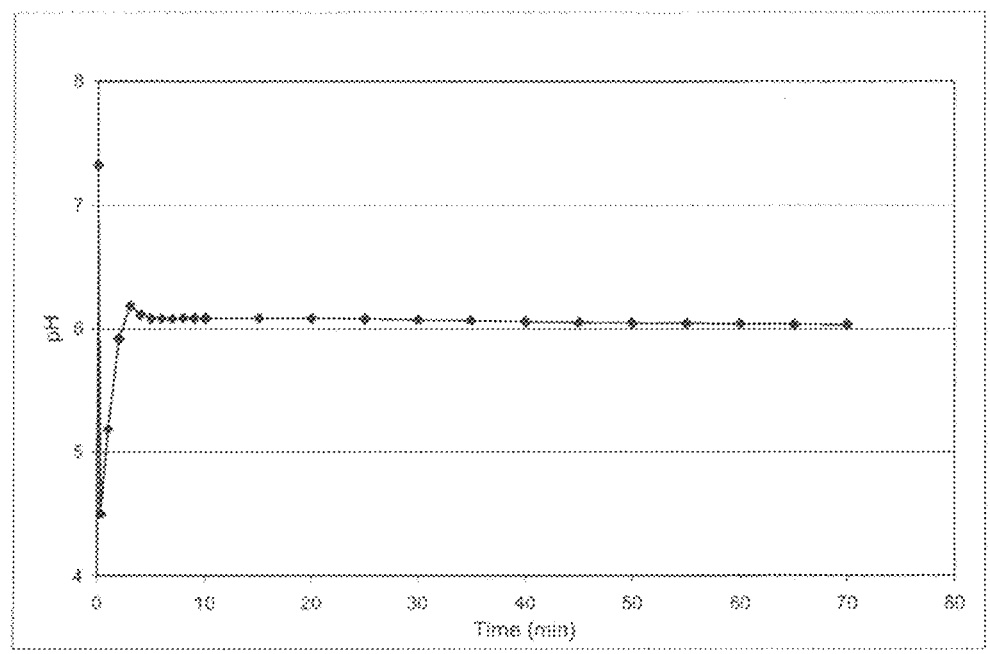
FIG. 13 shows the effect on pH of bulk addition of acid to nitrite.

The results can be seen in FIGS. 12 and 13.

In Example 16, the initial pH of sodium nitrite solution was measured to be approximately 7.35. The pH drops sharply to a level between 4.2 and 4.7 and then recovers rapidly (within 4-5 minutes) to a more stable value of ~6 after each addition. In some instances the pH recovery is so rapid that it produces an overshoot before falling back to the stable value.

In Example 17, the stable pH level that is achieved after mixing the reagents for 5 minutes is well above the physiologically tolerable level of 5.0 (the pH of saline) for oral-gastric-digestive delivery.

Example 18

Raman spectroscopy measurements were taken for the reaction of 6 ml of 1M Ascorbic Acid with 12 ml of 1M Sodium Nitrite. The reagents and solutions were as for Examples 16 and 17.

The reactive mixtures and the end products were measured using a Nicolet Almega XR; dispersive Raman spectrometer equipped with both macro- and microscope entrances. Spectra were excited with an externally stabilised near-infrared (NIR 785 nm) laser diode. Measurements are done with a slit width of 25 µm and spectral resolution is 4 $cm^{-1}$. A software system (Omnic, ver. 7.2a) was used to display and collect the data. Liquid or crystalline samples to be analysed were placed in a small quartz tube that fits into a sample holder and aligned with the laser beam.

The acid was added to the nitrite solution while the mixture was stirred at a constant rate of 60 rpm. A small amount (approximately 0.07 ml) of the mixture is taken out for spectroscopic analysis at varying intervals.

Figure 14:
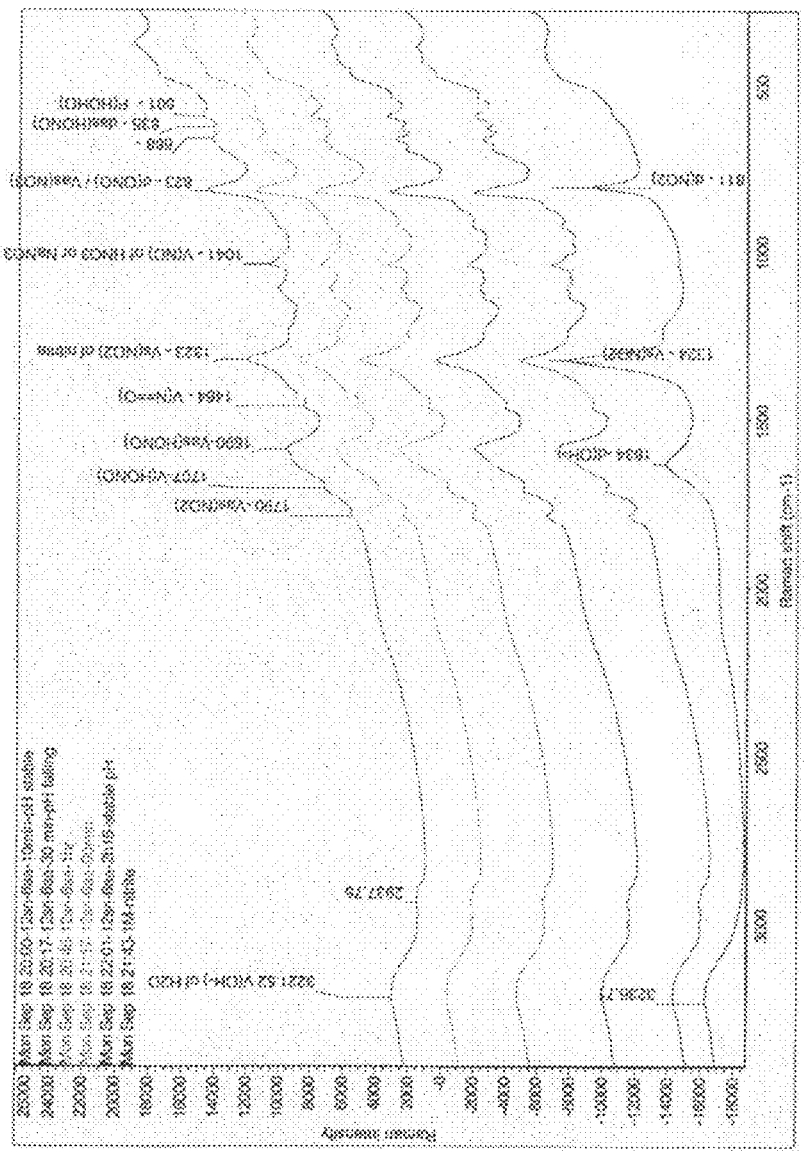
FIG. 14 shows a series of Raman spectra following addition of acid to nitrite.
Figure 15A:
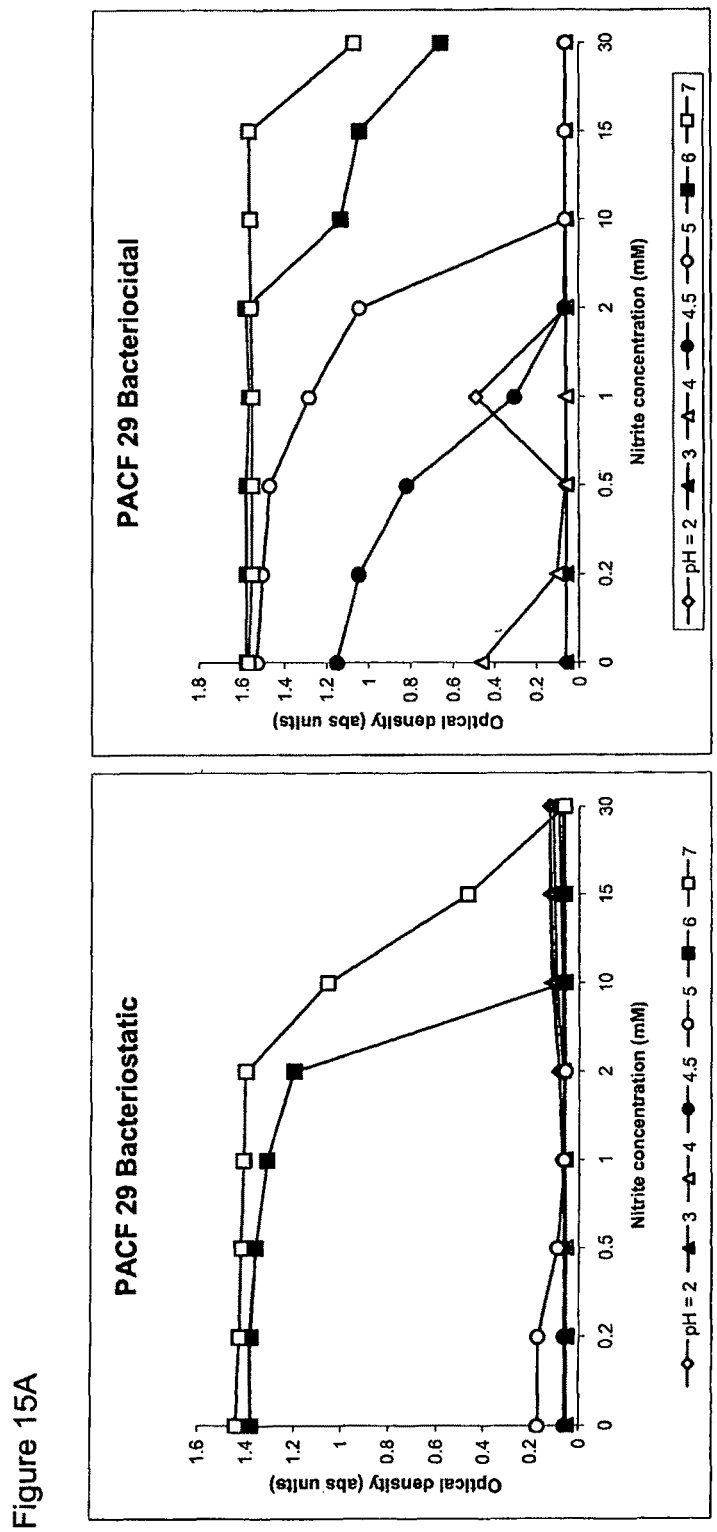
FIG. 15 shows the bacteriostatic and bacteriocidal properties of a mixture of oxides of nitrogen on various bacteria.
Figure 15B:
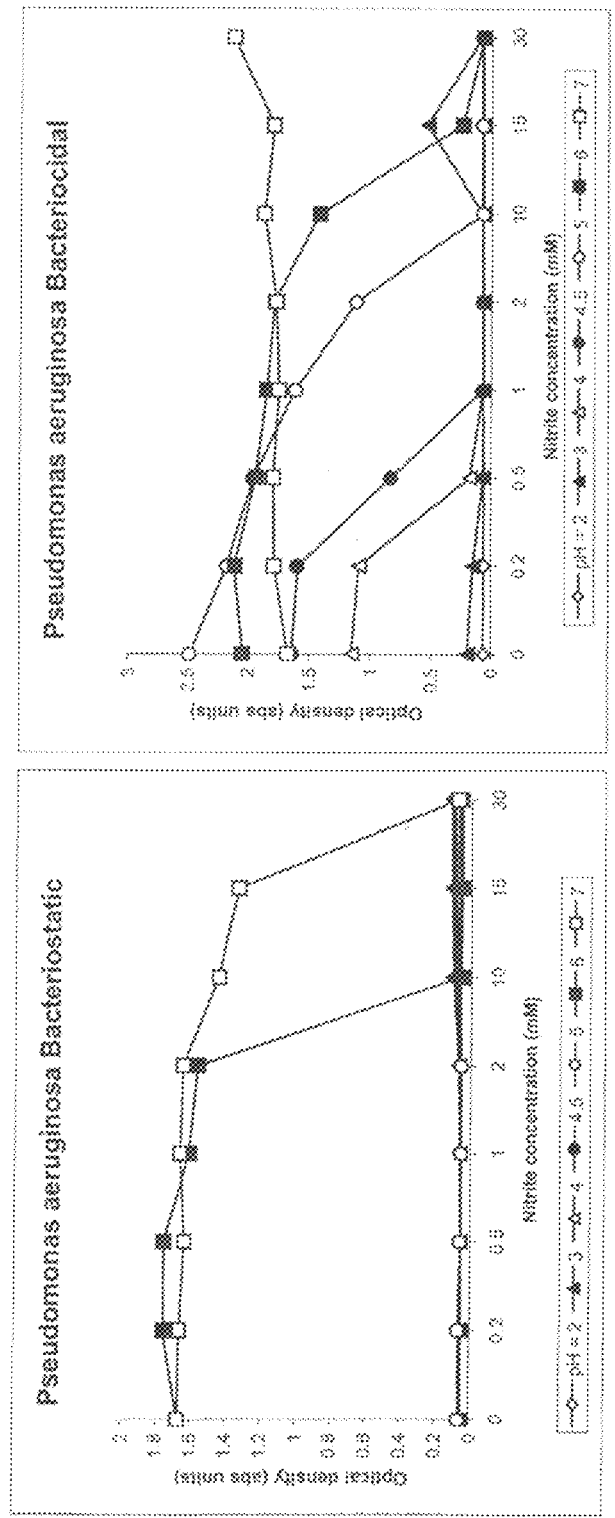
Figure 15C:
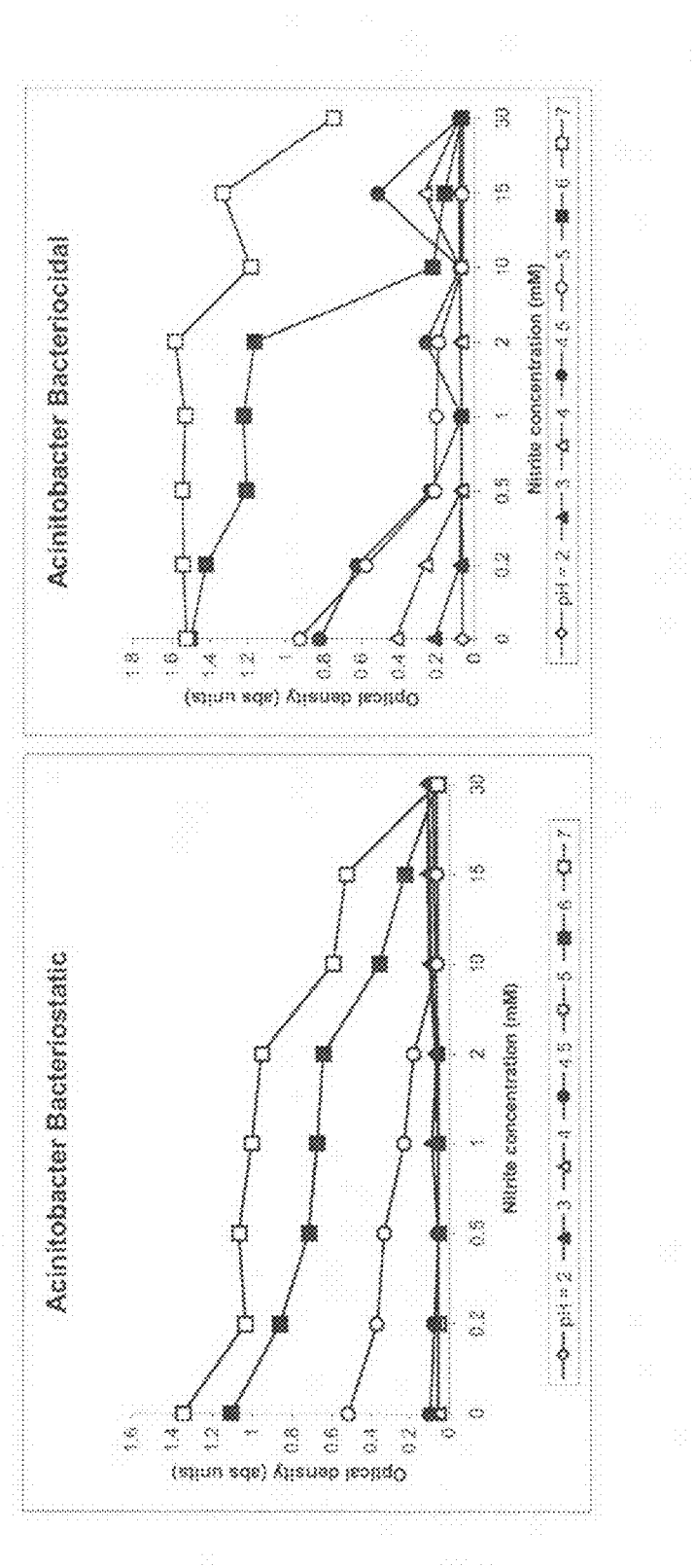
Figure 15D:
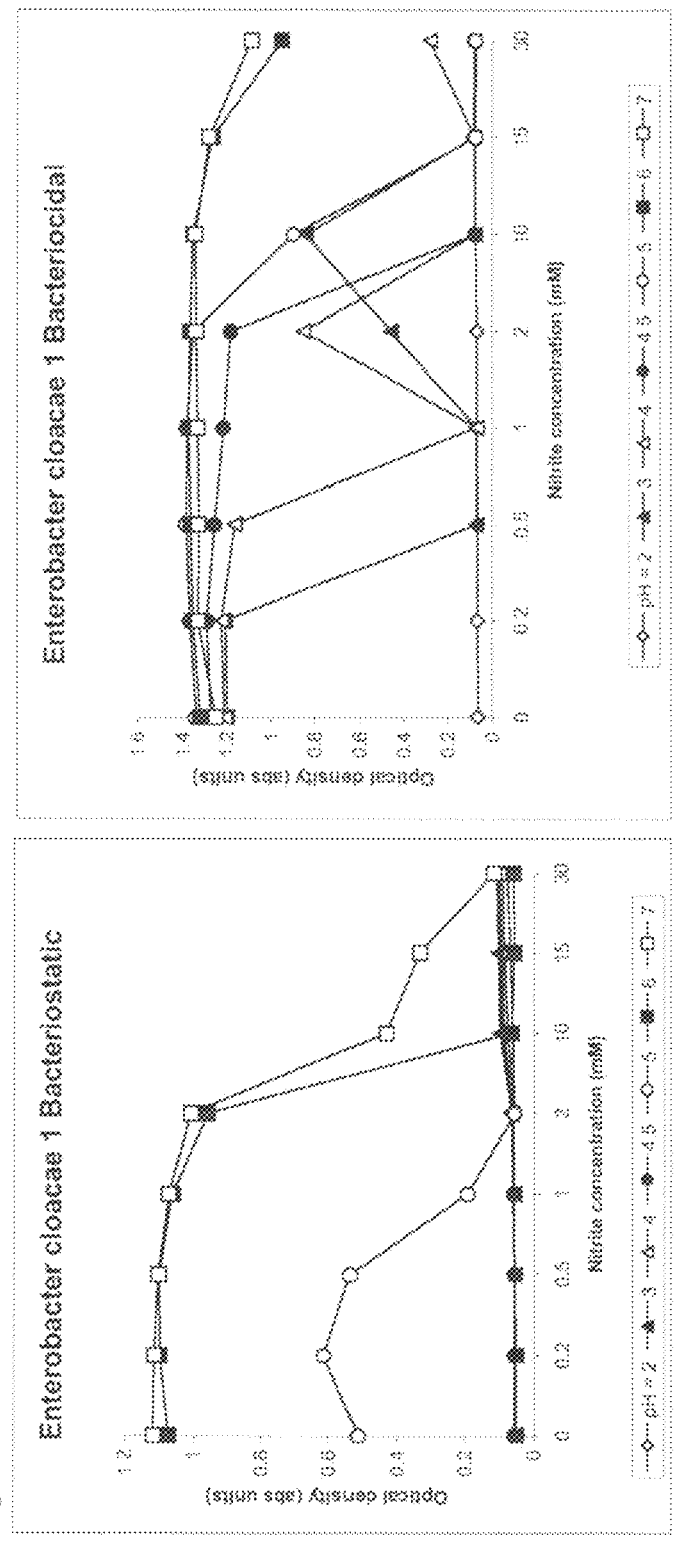
Figure 15E:
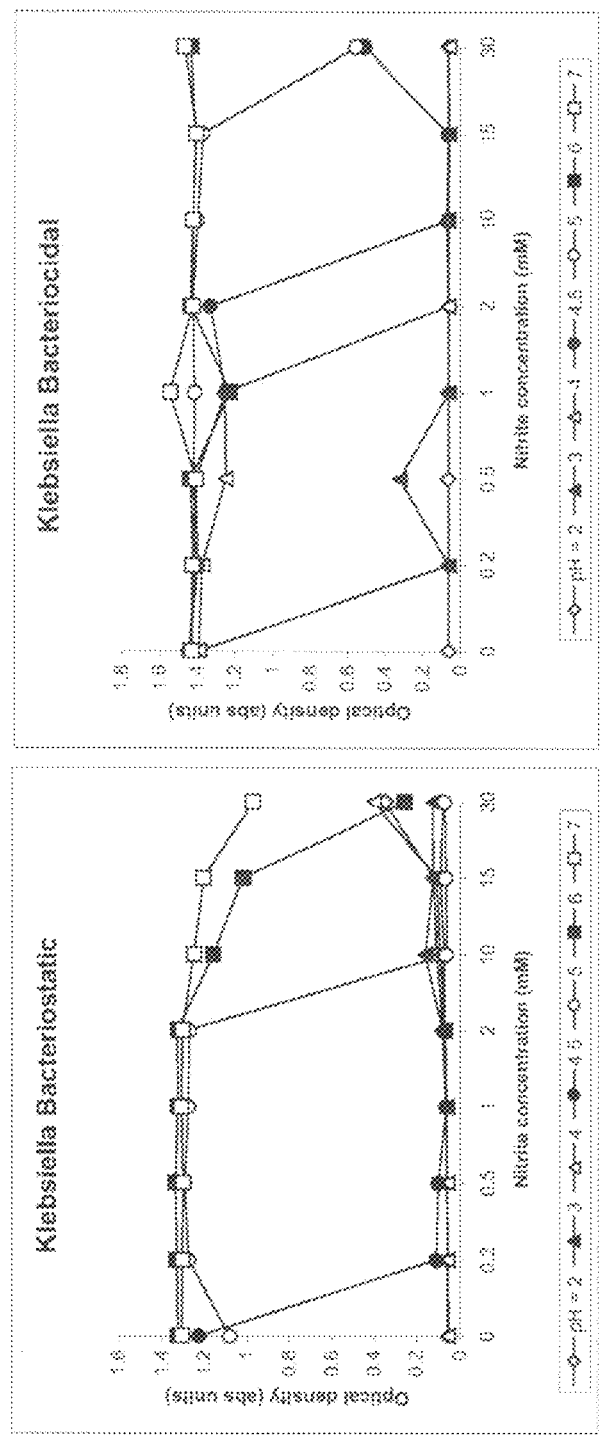
Figure 15F:
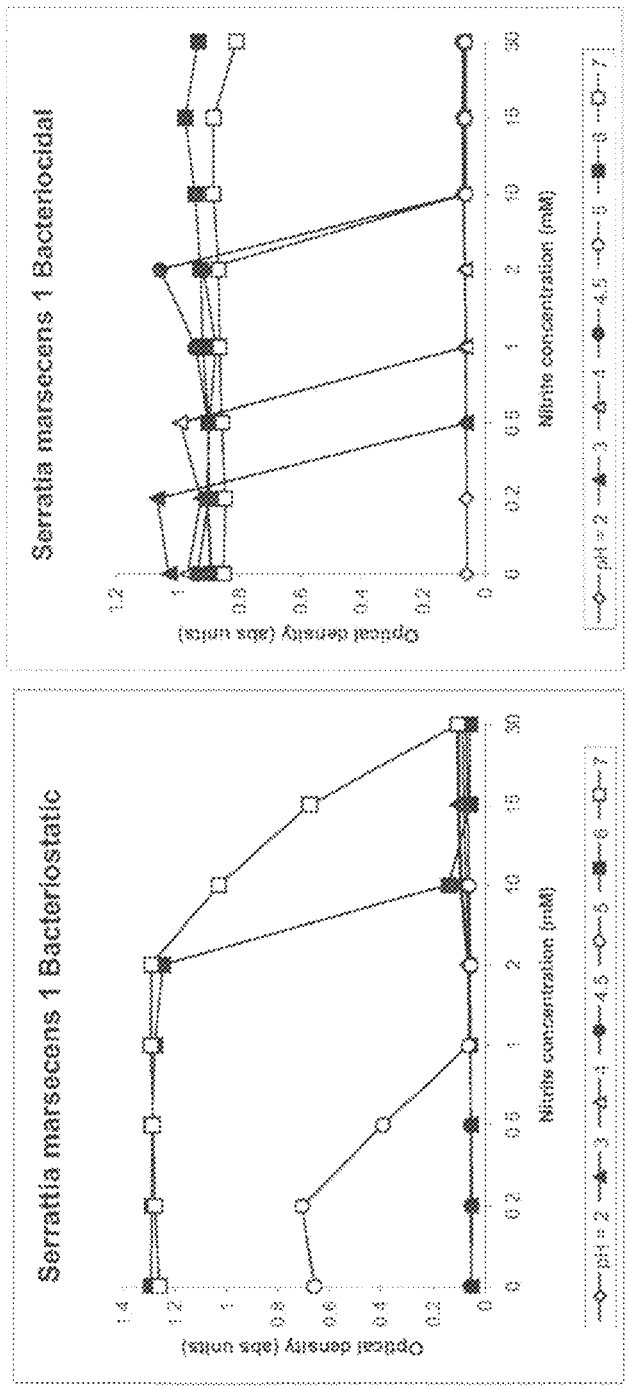
Figure 15H:
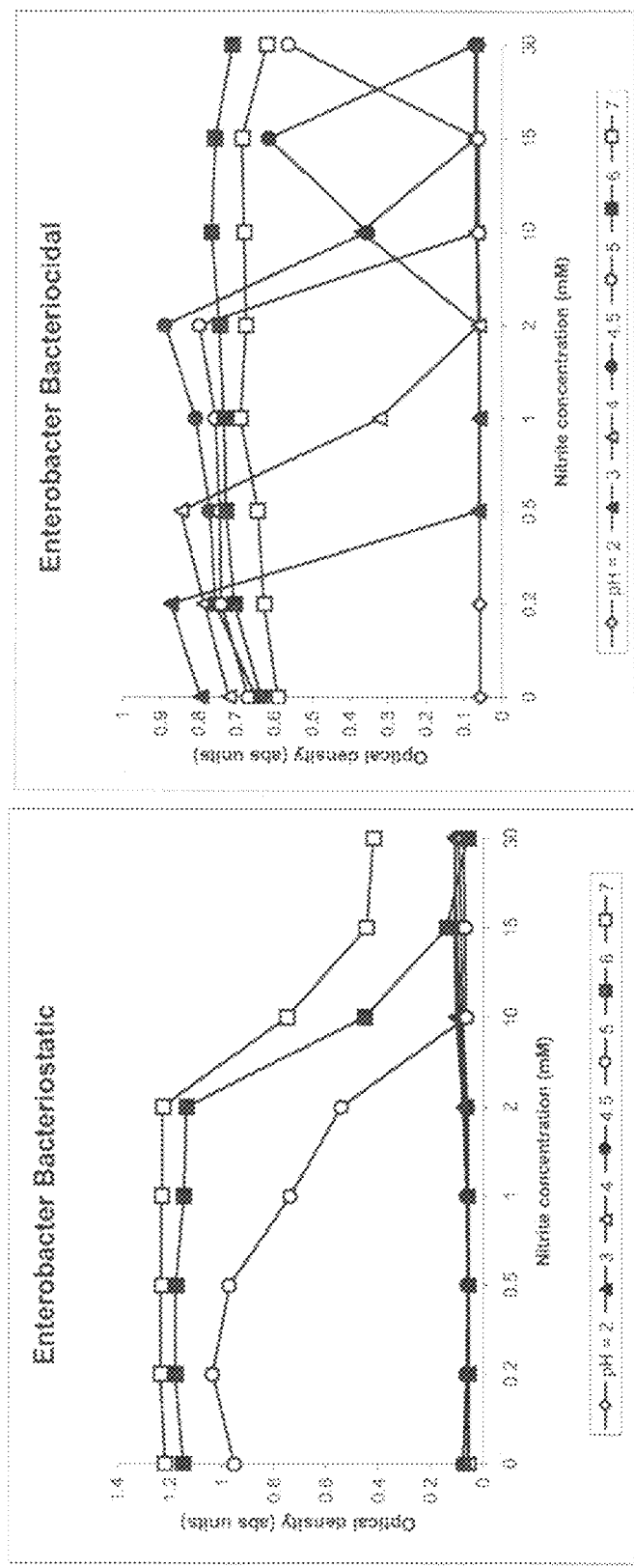
Figure 15I:
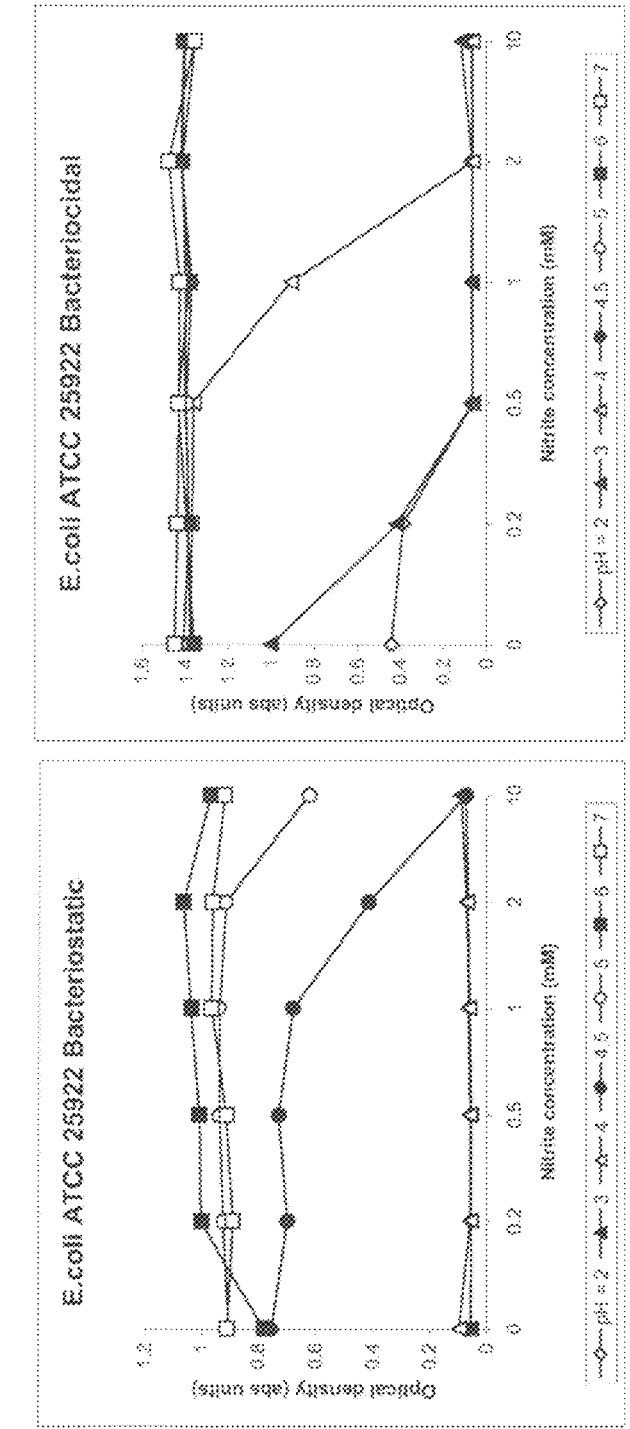
Figure 15J:
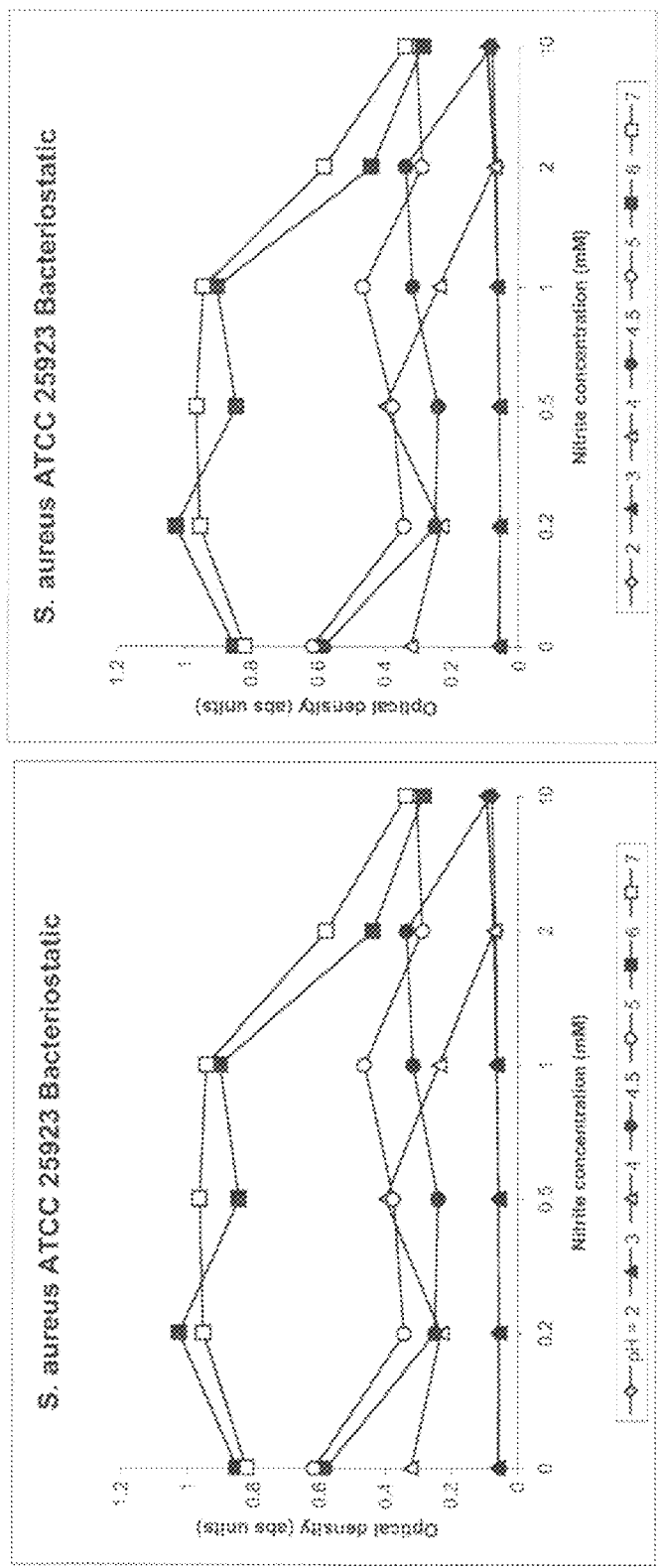
Figure 15K:
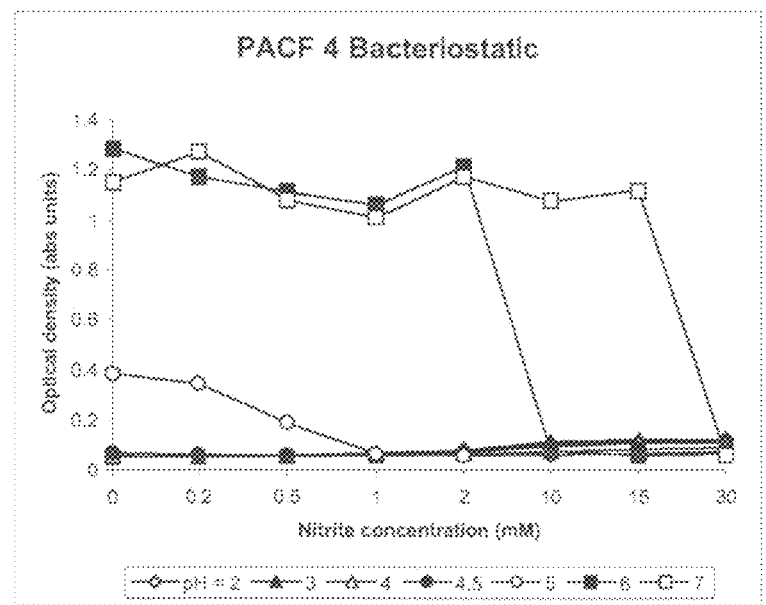
Figure 15L:
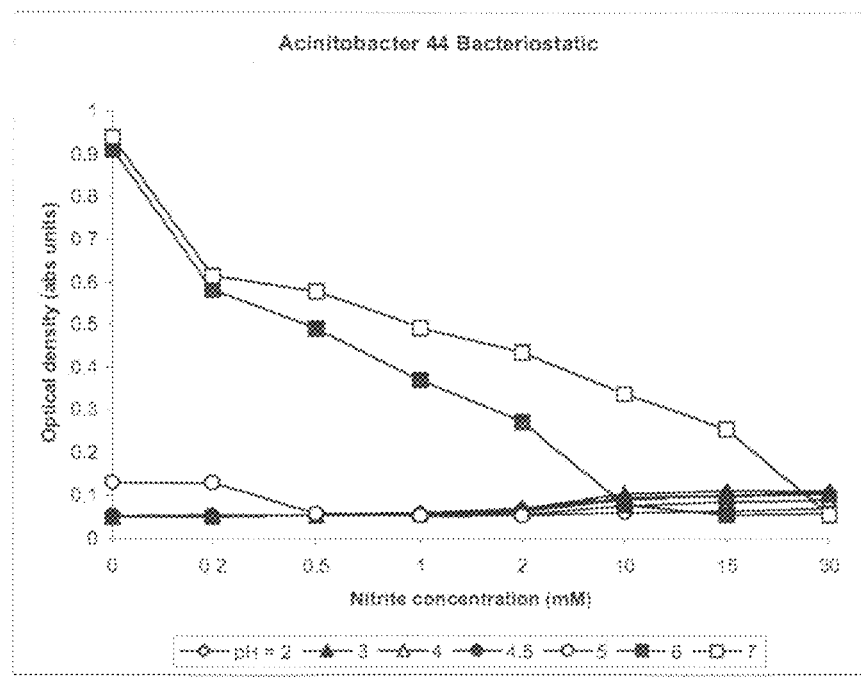
Figure 15M:
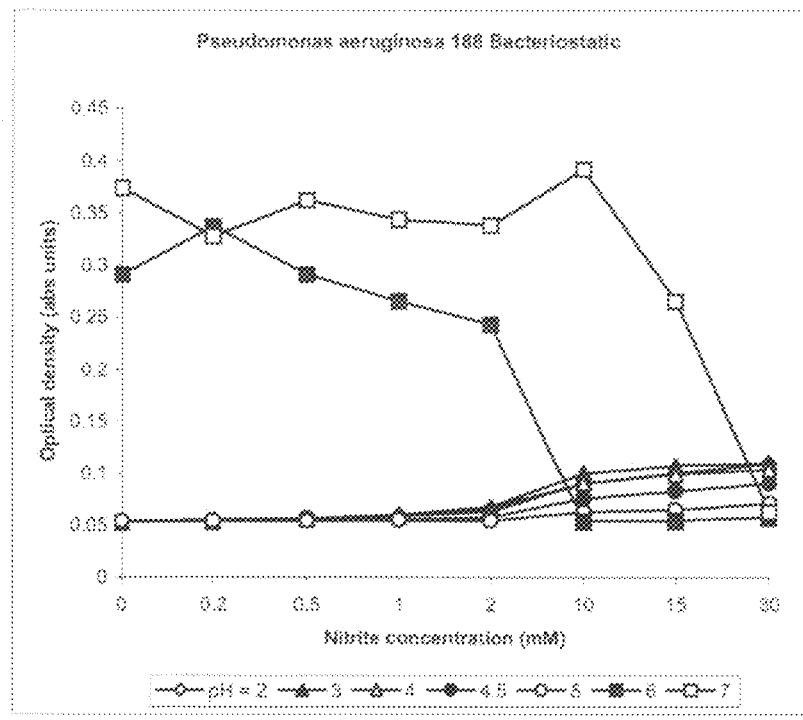
Figure 15N:
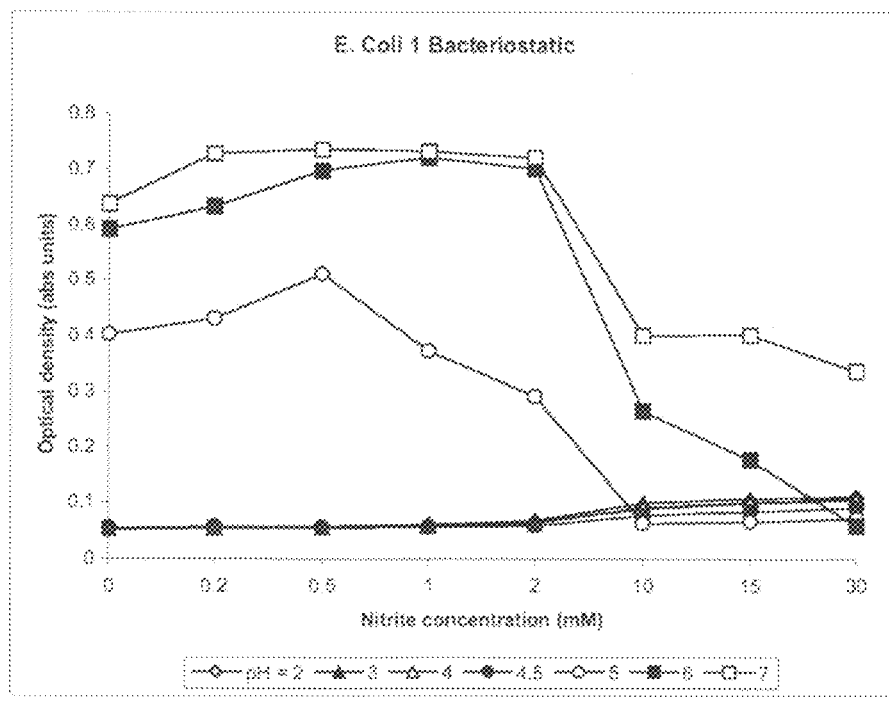

Spectra were taken at 10, 30, 60, 90 and 135 minutes from the time the reactants were mixed as well as after all reaction was complete. FIG. 14 shows the spectrum of sodium nitrite solution along with the spectra obtained during the reaction of 6 ml of acid with 12 ml of nitrite solution. The lower trace belongs to a sodium nitrite only solution.

The absence of any peak at all, in the 2250-2050 $cm^{-1}$ region indicates the absence of any hazardous ionic cyanide (like NaCN), cyanato (OCN) or fulminato (CNO) compounds in the mixture. For example, the stretching (CN) vibration produces a sharp band located in the region 2250-2050 $cm^{-1}$.

Measurements of the strong symmetric stretching vibration at 1325 $cm^{-1}$, ($V_s(NO_2)$ of sodium nitrite), reveals that half of the nitrite is reduced by the acid in less than 10 minutes. The amount of nitrite in the mixture was observed to show a further 8% decrease during the next 2 hours of observation. When the reaction was complete only about 31% of the initial amount of nitrite was left in the mixture.

This demonstrates that following a reaction, a solution with an excess nitrite to acid ratio retains sufficient nitrite to enable further NO/NOx generation reactions in vivo should the internal environment retain a low pH. Such reactions will augment the local availability of the NO—NOx reaction products and aid in local in vivo deactification of the tissues.

The Raman bands of an acidified nitrite solution are shown in Table 1. Table 2 shows the peak areas of Raman bands of acidified nitrite solution recorded at the times indicated.

TABLE 1

| Band Position | Assignment |
| --- | --- |
| 1791 cm-1 | Vas(NO2) |
| 1704 cm-1 | V(HONO) |
| 1590 cm-1 | Vas(NO2) of HONO |
| 1467 cm-1 | V(N=O), Vs(NO2) |
| 1325 cm-1 | Vs(NO2) of NaNO2 |
| 1041 cm-1 | V(NO) of NO3- of HNO3 or NaNO3 |
| 827 cm-1 | d(ONO), Vas(NO3) |
| 600 cm-1 | in-plane bending of HONO |

TABLE 2

| Band Position | Peak Area | | | | | |
| --- | --- | --- | --- | --- | --- | --- |
| | 10 min | 30 min | 60 min | 90 min | 135 min | End prod. |
| 1791 cm-1 | 1378 | 1159 | 766 | 606 | 374 | — |
| 1704 cm-1 | 903 | 828 | 449 | — | 495 | 256 |
| 1590 cm-1 | 5839 | 5416 | 4525 | 4739 | 4264 | 3934 |
| 1467 cm-1 | 934 | 855 | 720 | 632 | 659 | — |
| 1325 cm-1 | 6359 | 6161 | 5860 | 5944 | 5655 | 3967 |
| 1041 cm-1 | 2501 | 2109 | 2084 | 2122 | 2202 | 2113 |
| 827 cm-1 | 7693 | 7302 | 6628 | 6647 | 6170 | 4387 |
| 600 cm-1 | 2041 | 1842 | 1479 | 1334 | 923 | 921 |

After more than 2 hours observation there was still a considerable amount of gas bubbles evolving from the mixture. The stirring was stopped and the mixture was kept overnight. After 24 hours no more gas bubbles were observed and Raman spectra of the left over solution (end product) revealed that the concentration of nitrite had reduced to two third its concentration at 10 minutes (or, one third of its initial concentration before the reaction).

Example 19

A simple viability assay was used to determine if a standard laboratory strain of *M. tuberculosis* was susceptible to NO/NOx-mediated killing.

*M. tuberculosis* was cultured in 10 ml of standard medium (Middlebrook 7H9, 0.05% Tween 80, 10% v/v OADC supplement). For NO/NOx exposure, 1 ml of culture was inoculated into 10 ml of the Middlebrook solution plus 0.1 ml of a mixture of 0.5M $NaNO_2$ and 0.25M ascorbic acid. A control without the nitrite/ascorbic acid solution was set up.

Cultures were incubated at 37° C., standing for 24 hours. Serial dilutions were plated on solid medium (Middlebrook 7H10, 10% v/v OADC) and CFUs recorded after 3 weeks.

The pH of the medium was not significantly reduced by addition of the nitrite/ascorbic acid solution.

Colony forming unit (CFU) counts from the control culture were $1.5\times10^7$ per ml. There were no viable bacteria from the NO-treated culture at the lowest dilution plated (limit of detection 10 CFU/ml).

The NO-generating nitrite/ascorbic acid solution was effective in killing>6 logs of *M. tuberculosis* in 24 hours.

Example 20

An assay was used to determine the susceptibly of a number of different bacteria to NO/NOx-mediated killing.

Experiments were carried out in 96 microwell plates. A number of the microwells were filled with 60 μl of sodium nitrite to give final concentrations of 0, 0.2, 0.5, 1, 2, 10, 15, and 30 mM. Sixty μl of bacterial suspension (density of $2\times10^7$ colony-forming units per ml) and 120 μl of Brain Heart Infusion broth (Oxoid, Basingstoke, UK) acidified with hydrochloric acid to give final pH values of 2.0, 3.0, 4.0, 4.5, 5.0, 6.0 and 7.0 were also added.

The plates were sealed and incubated over night at 37° C. The inhibitory effect of acidified nitrite on bacterial growth was determined by measurement of the optical density (540 nm) of the wells using a microwell plate reader (Anthos ht III, Salzburg, Austria).

All experiments were carried out in triplicate.

To determine bactericidal activity after exposure to acidified nitrite, 60 μl of the bacterial suspension was transferred to 180 μl of a recovery media (Brain Heart Infusion broth; pH 7.0). Assessment of microbial growth was determined with the microwell plate reader to measure the optical density as above.

The effect of this mixture was tested on microorganisms previously isolated from patients. The results are shown in FIG. 15*a-n*.

It can be seen that the acidified nitrite solution has a bacteriostatic as well as bactericidal effect on various bacterial isolates.

The solution can be used for treatment of various conditions, as it is active against antibiotic resistant organisms, does not encourage the emergence of resistant strains and is effective over a wide pH range.

The invention claimed is:

1. A method of preventing ventilator associated pneumonia comprising applying a liquid formulation comprising a clinically effective amount of nitric oxide dissolved and/or dispersed therein to at least one of the oropharynx, the gastric system and the digestive system of a patient on a ventilator.

2. The method according to claim 1, wherein the liquid formulation contains from 10 to 40,000 parts per billion of nitric oxide.

3. The method according to claim 2, wherein the liquid formulation contains from 100 to 10,000 parts per billion of the nitric oxide.

4. The method according to claim 1, wherein the liquid formulation is an aqueous formulation.

5. The method according to claim 1, wherein the liquid formulation comprises the reaction product of at least one alkali metal, nitrite and/or at least one alkaline earth metal nitrite with at least one acid.

6. The method according to claim 5, wherein the liquid formulation comprises the reaction product of at least one alkali metal nitrite with ascorbic acid.

7. The method according to claim 1, wherein the liquid formulation additionally comprises at least one nutrient.

8. The method according to claim 1, wherein the liquid formulation is applied to the oropharynx.

9. The method according to claim 1, wherein the liquid formulation is applied to the gastric system.

10. The method according to claim 1, wherein the liquid formulation is applied to the digestive system.

11. The method according to claim 1, wherein the liquid formulation is applied to the mouth.

* * * * *